US011801153B2

(12) United States Patent
Bulea et al.

(10) Patent No.: US 11,801,153 B2
(45) Date of Patent: Oct. 31, 2023

(54) POWERED GAIT ASSISTANCE SYSTEMS

(71) Applicant: The United States of America, as represented by the Secretary, Department of Health and Human Services, Bethesda, MD (US)

(72) Inventors: Thomas Bulea, Silver Spring, MD (US); Zachary Lerner, Bethesda, MD (US); Diane Damiano, Bethesda, MD (US); Andrew Gravunder, Gaithersburg, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 779 days.

(21) Appl. No.: 16/321,565

(22) PCT Filed: Jul. 31, 2017

(86) PCT No.: PCT/US2017/044625
§ 371 (c)(1),
(2) Date: Jan. 29, 2019

(87) PCT Pub. No.: WO2018/023109
PCT Pub. Date: Feb. 1, 2018

(65) Prior Publication Data
US 2021/0298984 A1    Sep. 30, 2021

Related U.S. Application Data

(60) Provisional application No. 62/368,926, filed on Jul. 29, 2016.

(51) Int. Cl.
*A61F 2/70*     (2006.01)
*A63F 13/212*   (2014.01)
(Continued)

(52) U.S. Cl.
CPC .............. *A61F 2/70* (2013.01); *A61H 1/024* (2013.01); *A61H 3/00* (2013.01); *A63F 13/212* (2014.09);
(Continued)

(58) Field of Classification Search
CPC .. A61H 3/00; A61H 1/024; A61H 2201/1642; A61H 2201/5061;
(Continued)

(56) References Cited

U.S. PATENT DOCUMENTS 7,947,004 B2    5/2011  Kazerooni et al.
2008/0009771 A1*  1/2008  Perry ................... A61H 1/0281
                                                600/587
(Continued)

FOREIGN PATENT DOCUMENTS

BR     112013009760     7/2016

OTHER PUBLICATIONS

Bartole et al., "The H2 robotic exoskeleton for gait rehabilitation after stroke: early findings from a clinical study," *Journal of Neuroengineering and Rehabilitation*, 14 pages (Jun. 17, 2015).
(Continued)

*Primary Examiner* — Philip R Wiest
*Assistant Examiner* — Nathan M Le
(74) *Attorney, Agent, or Firm* — Leydig, Voit & Mayer, Ltd.

(57) ABSTRACT

Disclosed are powered gait assistance systems that include a controller, sensors, and a motor coupled to a patient's thigh and lower leg and operable to apply assistive torque to the patient's knee joint to assist the patient's volitional knee pivoting muscle output during selected stages of the patient's gait cycle, such that the assistive torque applied by the motor improves the patient's leg posture, muscle output, range of motion, and/or other parameters over the gait cycle.
(Continued)

The sensors can include a torque sensor that measures torque applied by the motor, a knee angle sensor, a foot sensor that measures ground contact of the patient's foot, and/or other sensors. The controller can determine what stage of the patient's gait cycle the patient's leg is in based on sensor signals and cause the motor to apply corresponding assistive torque to the knee based on the gait cycle stage, sensor inputs, and known patient characteristics.

22 Claims, 21 Drawing Sheets

(51) Int. Cl.
  *A61H 1/02* (2006.01)
  *A61H 3/00* (2006.01)
(52) U.S. Cl.
  CPC .............. *A61H 2201/1642* (2013.01); *A61H 2201/5012* (2013.01); *A61H 2201/5061* (2013.01); *A61H 2201/5069* (2013.01); *A61H 2201/5097* (2013.01); *A61H 2230/605* (2013.01)
(58) Field of Classification Search
  CPC ...... A61H 2201/5069; A61H 2201/605; A61H 2201/165; A61F 2/70
  See application file for complete search history.

(56) References Cited

U.S. PATENT DOCUMENTS

| | | | |
|---|---|---|---|
| 2008/0039756 A1* | 2/2008 | Thorsteinsson | A61F 5/0123 600/595 |
| 2008/0161937 A1* | 7/2008 | Sankai | A61B 5/24 623/25 |
| 2010/0113980 A1* | 5/2010 | Herr | A61F 2/60 600/587 |
| 2010/0121232 A1 | 5/2010 | Sankai | |
| 2010/0312363 A1* | 12/2010 | Herr | A61F 2/64 623/39 |
| 2011/0066088 A1 | 3/2011 | Little et al. | |
| 2011/0112447 A1* | 5/2011 | Hsiao-Wecksler | A61H 3/008 601/33 |
| 2012/0059432 A1* | 3/2012 | Emborg | A61N 1/36034 607/49 |
| 2012/0101415 A1 | 4/2012 | Goffer et al. | |
| 2012/0165158 A1* | 6/2012 | Ren | A63B 71/0622 482/7 |
| 2013/0226048 A1 | 8/2013 | Unluhisarcikli et al. | |
| 2014/0142475 A1 | 5/2014 | Goldfarb et al. | |
| 2014/0364962 A1* | 12/2014 | Gregg | A61F 2/6607 623/24 |
| 2015/0142130 A1* | 5/2015 | Goldfarb | A61H 1/0244 623/25 |
| 2015/0190249 A1* | 7/2015 | Ishibashi | A61H 1/0244 623/24 |
| 2015/0366740 A1* | 12/2015 | Endo | A61H 1/0244 623/24 |
| 2015/0374573 A1* | 12/2015 | Horst | F16H 19/0628 74/89.22 |
| 2016/0331560 A1* | 11/2016 | Tong | A61H 1/024 |
| 2017/0196750 A1* | 7/2017 | Hepler | F03G 7/08 |

OTHER PUBLICATIONS

Esquenazi et al., "The ReWalk Powered Exoskeleton to Restore Ambulatory Function to Individuals with Thoracic-Level Motor-Complete Spinal Cord Injury," *American Journal of Physical Medicine & Rehabilitation*, 11 pages (Nov. 2012).

Farris et al., "Preliminary Evaluation of a Powered Lower Limb Orthosis to Aid Walking in Paraplegic Individuals," *IEEE Trans, Neural Syst. Rehabil. Eng.*, 19(6):652-659 (Dec. 2011).

International Search Report and Written Opinion for related International Application No. PCT/US2017/044625, dated Nov. 14, 2017, 9 pages.

* cited by examiner

Kinematic, Muscle Activity, and Spatio-Temporal Parameters from the Clinical Evaluation of the Exoskeleton

| | Baseline AFO | | Free | | Powered | |
|---|---|---|---|---|---|---|
| | R | L | R | L | R | L |
| Number of Gait Cycles | 3 | 4 | 4 | 5 | 4 | 4 |
| Max Knee Flexion Angle Stance (°) | 56.0 (6.5) | 49.7 (2.8) | 54.1 (3.4) | 48.1 (2.6) | 37.4 (3.6) | 37.8 (1.8) |
| Peak Knee Extension Angle Stance (°) | 41.3 (5.3) | 31.4 (3.4) | 42.6 (1.7) | 29.8 (3.2) | 23.2 (4.7) | 19.9 (3.0) |
| Knee Range of Motion (°) | 32.3 (10.1) | 34.4 (6.5) | 32.5 (5.8) | 36.5 (7.6) | 47.6 (4.4) | 55.4 (8.9) |
| Max Hip Extension Angle (°) | 2.0 (5.4) | 3.6 (3.7) | 6.3 (3.1) | 6.1 (3.7) | -3.4 (3.3) | -2.3 (2.4) |
| Max Ankle Dorsi-Flexion Angle (°) | 22.1 (0.6) | 14.2 (0.3) | 32.4 (1.1) | 30.3 (1.5) | 41.4 (2.7) | 26.0 (2.4) |
| Step Length (cm) | 32.9 (1.8) | 35.0 (6.1) | 25.5 (4.5) | 25.8 (6.5) | 22.3 (5.3) | 27.3 (3.4) |
| Step Width (cm) | 18.4 (4.3) | 21.3 (7.9) | 16.8 (2.1) | 16.3 (4.1) | 20.6 (2.6) | 19.6 (3.0) |
| Cadence (Steps/min) | 152 (3) | 135 (6) | 108 (17) | 106 (7) | 113 (14) | 98 (34) |

Value are Mean (SD). Bold Indicates a Significant Difference from the Baseline Condition ($p<0.05$).

FIG. 6

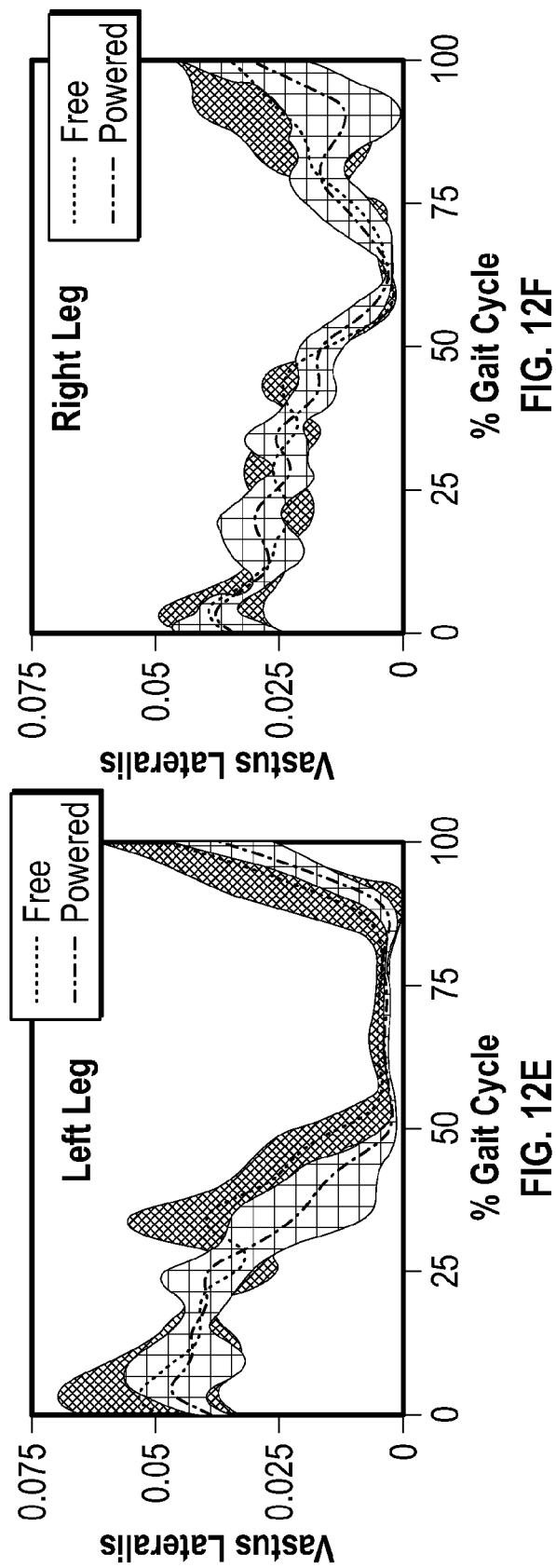
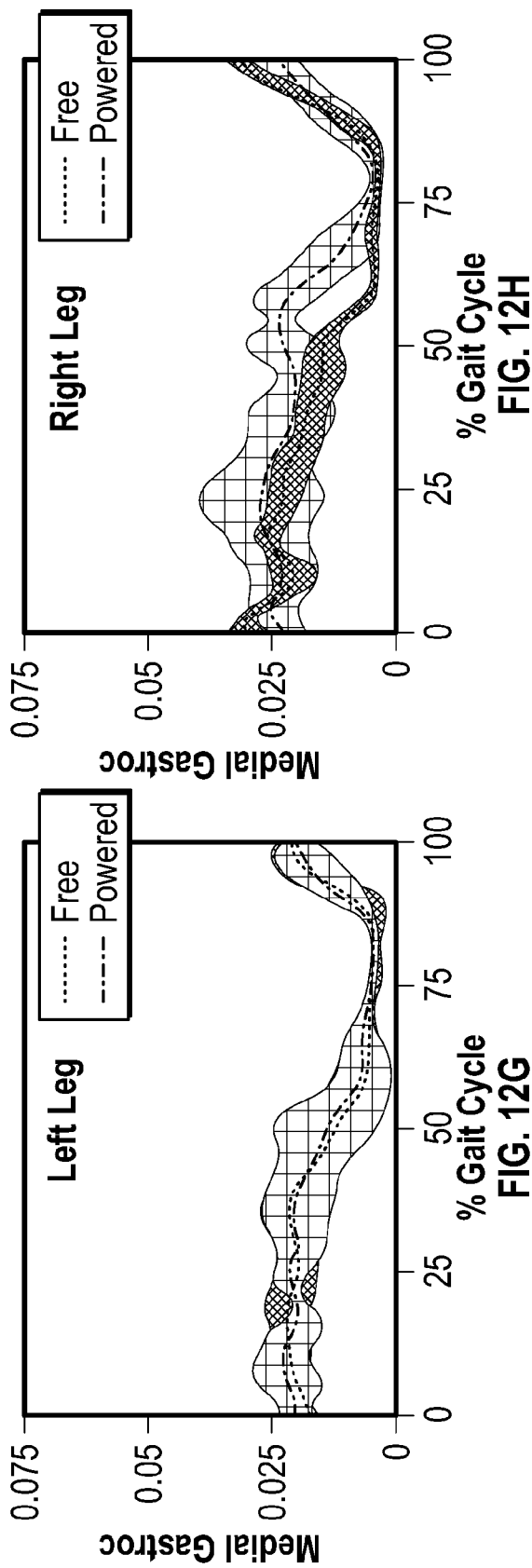
FIG. 12E
FIG. 12F
FIG. 12G
FIG. 12H

POWERED GAIT ASSISTANCE SYSTEMS

CROSS-REFERENCE TO RELATED APPLICATIONS

This application is the U.S. National Stage of International Application No. PCT/US2017/044625, filed Jul. 31, 2017, which claims the benefit of U.S. Provisional Application No. 62/368,926, filed Jul. 29, 2016, which is herein incorporated by reference in its entirety.

FIELD

This application is related to the field of powered systems for assisting human ambulation and other activities.

BACKGROUND

Cerebral palsy (CP) is a group of motor disabilities caused by a perinatal non-progressive injury to the central nervous system. CP is the most common pediatric motor disorder, affecting 2 to 3 per 1000 live births. Individuals with CP present a variety of disabilities including spasticity, rigidity and diminished coordination and motor control. Individuals with CP are often partitioned into subgroups based on the type and distribution of motor impairments. One of the most common subgroups is spastic diplegia, in which pathologic gait patterns are frequently observed. Crouch gait, which is characterized by excessive stance phase knee flexion and may be accompanied by other deficits at the hip and/or ankle, is one of the most frequently observed gait deviations. Crouch gait can lead to joint pain and degenerative arthritis due to elevated joint contact forces, bony deformities, and increased risk for falls from inadequate foot clearance. Additionally, crouch gait is less efficient than normal walking patterns and many experience deterioration of walking ability with age, leading to a loss of ambulation in a large portion of the population.

The most common treatments for crouch gait include surgery, botulinum toxin injections, physical therapy and strengthening, and orthotic interventions. Outcomes from surgical interventions, which typically target the hamstrings, are variable. Distal femoral extension osteotomy procedures have shown improvement of knee extension in short-term follow up, particularly when combined with patellar tendon advancement, offering a potentially effective but more invasive solution. One reason for the mixed surgical outcomes may be heterogeneity underlying the crouch gait pattern in diplegic CP. In addition to hamstring spasticity, anti-gravity (extensor) weakness contributes to the deterioration of walking capabilities as a function of age. However, like surgery, muscle strengthening programs have inconsistent outcomes. Achieving and maintaining adequate strength levels in individuals with motor disabilities is a challenging problem that is exacerbated because ambulatory children with CP are less active than children without disabilities. Orthotic bracing, aimed to increase mobility of individuals with crouch gait, may block or restrict motion at the ankle and or the knee joint to provide passive weight support or to suppress unwanted motions. Traditional and floor reaction ankle-foot orthoses (AFO and FRAFO, respectively) have been shown to temporarily improve knee extension and spatiotemporal gait parameters while worn. However, long term use can lead to greater weakness in the restricted muscle groups over time. Treadmill based robotic assisted therapy offers the advantage of repetitive practice. Improved function has been reported in pilot studies of treadmill based training in CP, but their overall effectiveness compared to traditional therapies of equal intensity is equivalent. Furthermore, these strategies are limited in the environment and duration in which they can be applied and have not been explicitly studied for remediation of crouch gait. Functional electrical stimulation (FES) devices have been applied to treat crouch gait in children with CP with limited success using percutaneous and surface electrodes to stimulate extensor muscles; however, the intensity of stimulation required to extend the flexed knee can be difficult to reach.

Thus, there is a clear need for more effective interventions which can preserve and/or augment strength on a continuous basis for those with crouch gait from CP.

SUMMARY

Disclosed herein are powered gait assistance systems (sometimes alternatively referred to as robotic systems or exoskeletons) that can function as mobility aids and as training devices. The disclosed systems can include a programmed controller, various sensors, and a torque applicator (e.g., a motor, spring, etc.) coupled to a patient's leg (e.g., at the upper hips, leg/thigh, lower leg/shank, and/or foot) and operable to apply assistive torque to the patient's leg joint(s) to assist the patient's volitional joint actuation muscle output during selected stages of the patient's gait cycle, such that the applied torque improves the patient's leg posture, muscle activity, joint actuation moment, range of motion, and/or other parameters over the gait cycle. The sensors can include a torque sensor that measures torque applied by the system at the joint(s), muscle output sensors to track volitional effort exerted by the patient, joint angle sensor(s), foot-located sensor(s) that measure ground contact of the patient's foot, and/or other sensors. The level of applied torque can be based on predetermined levels or can be determined in real-time based on data received from the sensors, etc. The controller can determine what stage of the patient's gait cycle the patient's leg is in based on sensor inputs and cause the torque applicator to apply corresponding assistive or resistive torque to the joint(s) based on the gait cycle stage, sensor inputs, known patient characteristics, and/or other factors.

Disclosed systems and methods can be particularly beneficial as a treatment for crouch gait, such as in in children with cerebral palsy (CP). The disclosed systems can be based on the architecture of a conventional orthotic device (e.g., a KAFO), can be lightweight, adjustable over time, and modular, making them suitable for growing and developing children. Moreover, the disclosed technology can help improve the patient's native ability to walk over time (e.g., by strengthening muscles, improving native muscle output, correcting posture, and/or improving coordination) such that the patient may eventually no longer need assistive devices to walk with a sufficiently "normal" and efficient gait pattern.

In some embodiments, the system includes a transmission system coupling a motor to the knee joint. The transmission can include a chain, gear, or cable transmission system for example. A chain or cable transmission can allow placement of the motor farther from the knee joint. A transmission system can also be used to increase the torque output of the motor or increase the angular velocity output of the motor, as needed for a particular application.

In some embodiments, the system can assist patient knee joint extension during a late swing phase of the gait cycle prior to foot touch down, can assist patient knee joint extension during a ground contact phase of the gait cycle prior to toe take off, and/or can assist patient knee joint flexion during an early swing phase of the gait cycle after toe take off. In some embodiments, the motor applies no assistive torque or resistance during one or more portions of the gait cycle, such as an early swing phase.

In various embodiments, the torque applicator can be located in several different locations and still be operable to apply assistive torque to the patient. For example, in some embodiments, a motor is positioned anterior to the patient's knee, in some embodiments, the motor is positioned lateral to the patient's thigh, and in some embodiments, the motor is positioned on the patient's torso or hips.

In some embodiments, the controller is programmed to wirelessly communicate with a remote computing system and/or a cloud based communication system. This can allow for remote communication with a clinician and/or active adjustments from a clinician or operator, for example. This can also allow the system to feedback data to a database and receive software and firmware updates. This can also allow heavy computational work to be performed remotely, minimizing the size and cost of the disclosed systems.

The powered gait assistance systems can also be used with or as part of a computerized gaming/training system. For example, the patient's leg motions can control action in a computer game or other displayed environment, such that the patient is encouraged to bend and extend his knees to make an object in the game/display move. The patient may also wear a virtual reality headset as part of the gaming/training system.

The foregoing and other objects, features, and advantages of the disclosed technology will become more apparent from the following detailed description, which proceeds with reference to the accompanying figures.

BRIEF DESCRIPTION OF THE DRAWINGS

FIG. 6 is a table showing comparative data for kinematic, muscle activity, and spatiotemporal parameters measured during clinical evaluation of an exemplary gait assistance system.

FIGS. 12A-12H show mean EMG linear envelopes (in mV) across the gait cycle for various leg muscles during free and powered system conditions. Shaded regions represent plus-minus one standard deviation from the mean.

DETAILED DESCRIPTION

Figure 1:
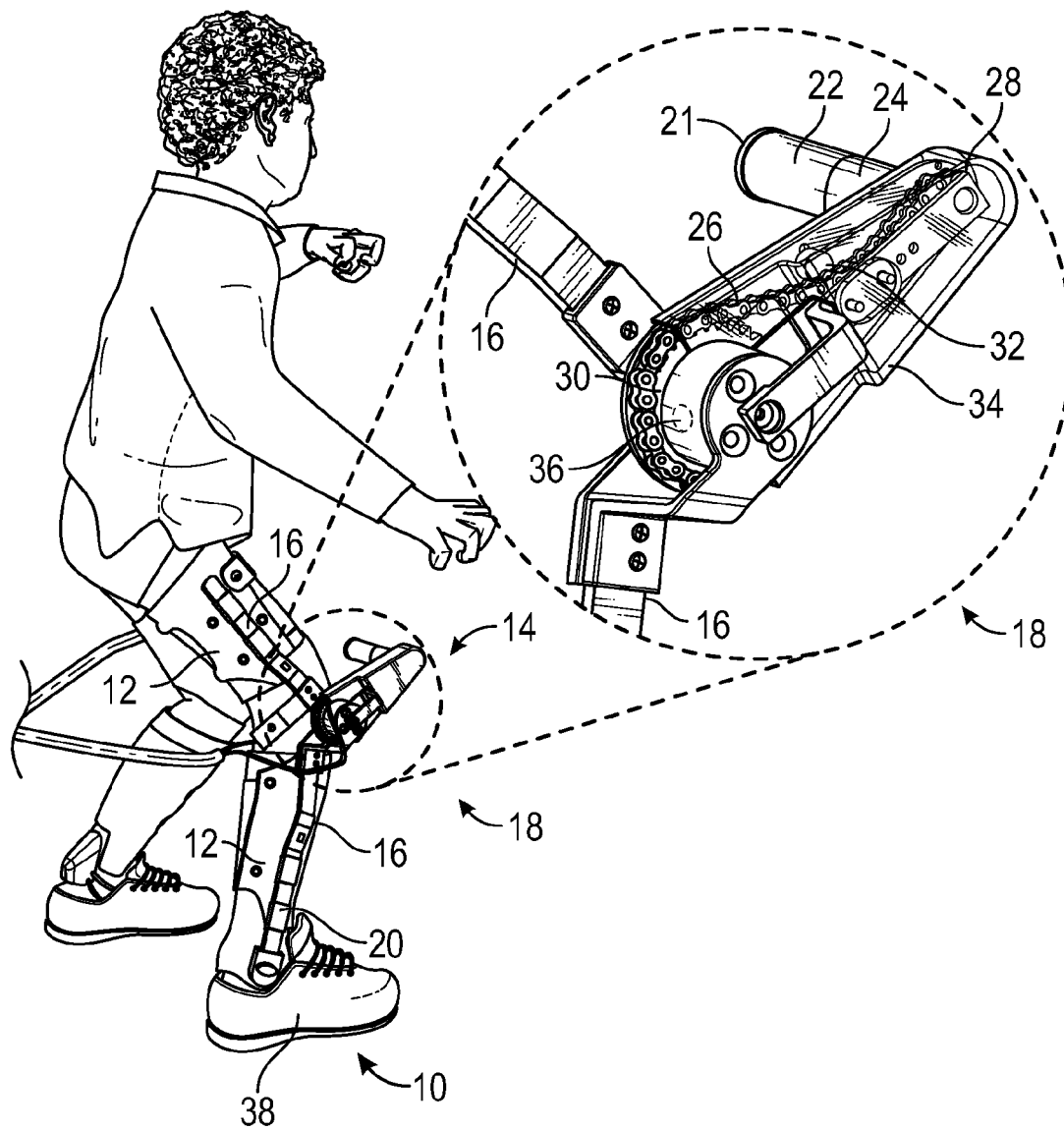
FIG. 1 shows a child with crouch gait wearing an exemplary gait assistance system comprising orthotic braces and motorized devices that provide assistive torque at the knees during selected portions of the gait cycle.
Figure 2:
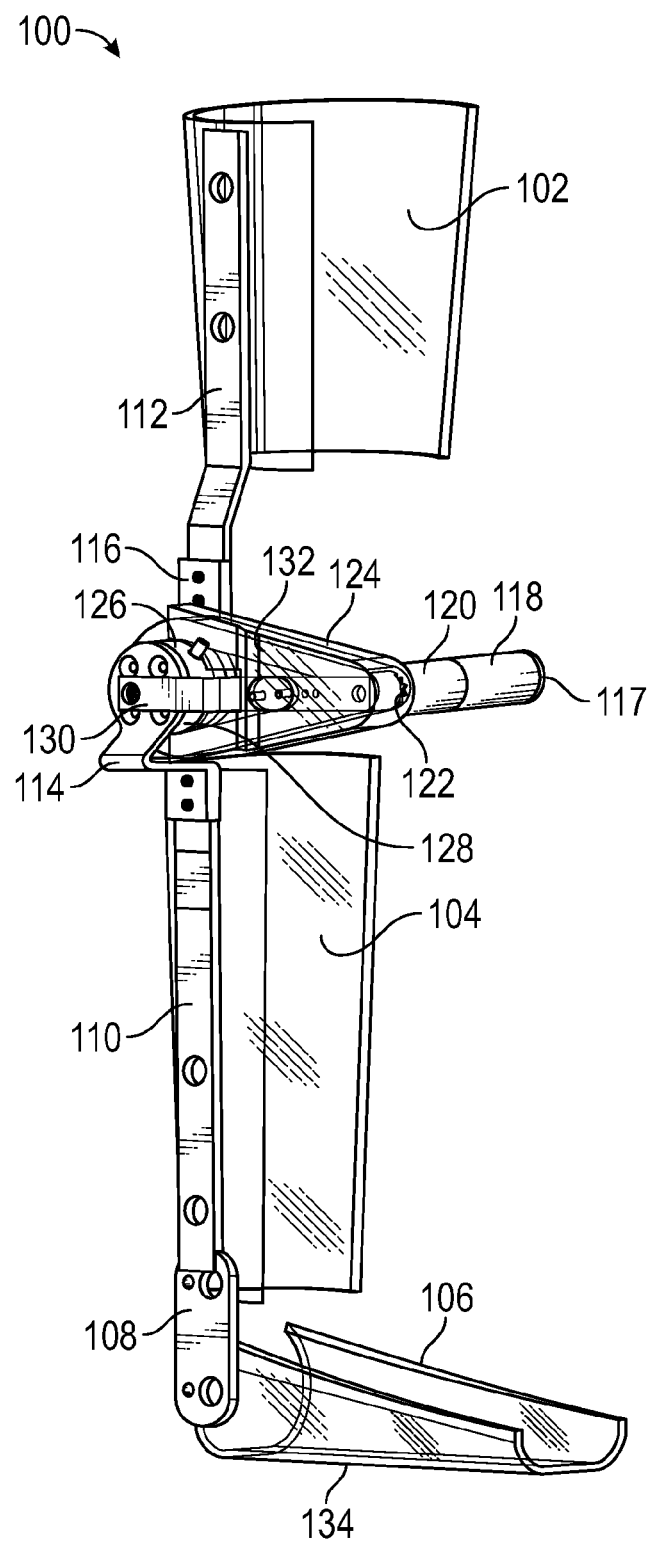
FIG. 2 is a lateral-anterior view of another exemplary gait assistance system comprising thigh, shank, and foot orthotics and a modular powered knee portion that provides assistive torque at the knee joint.
Figure 3:
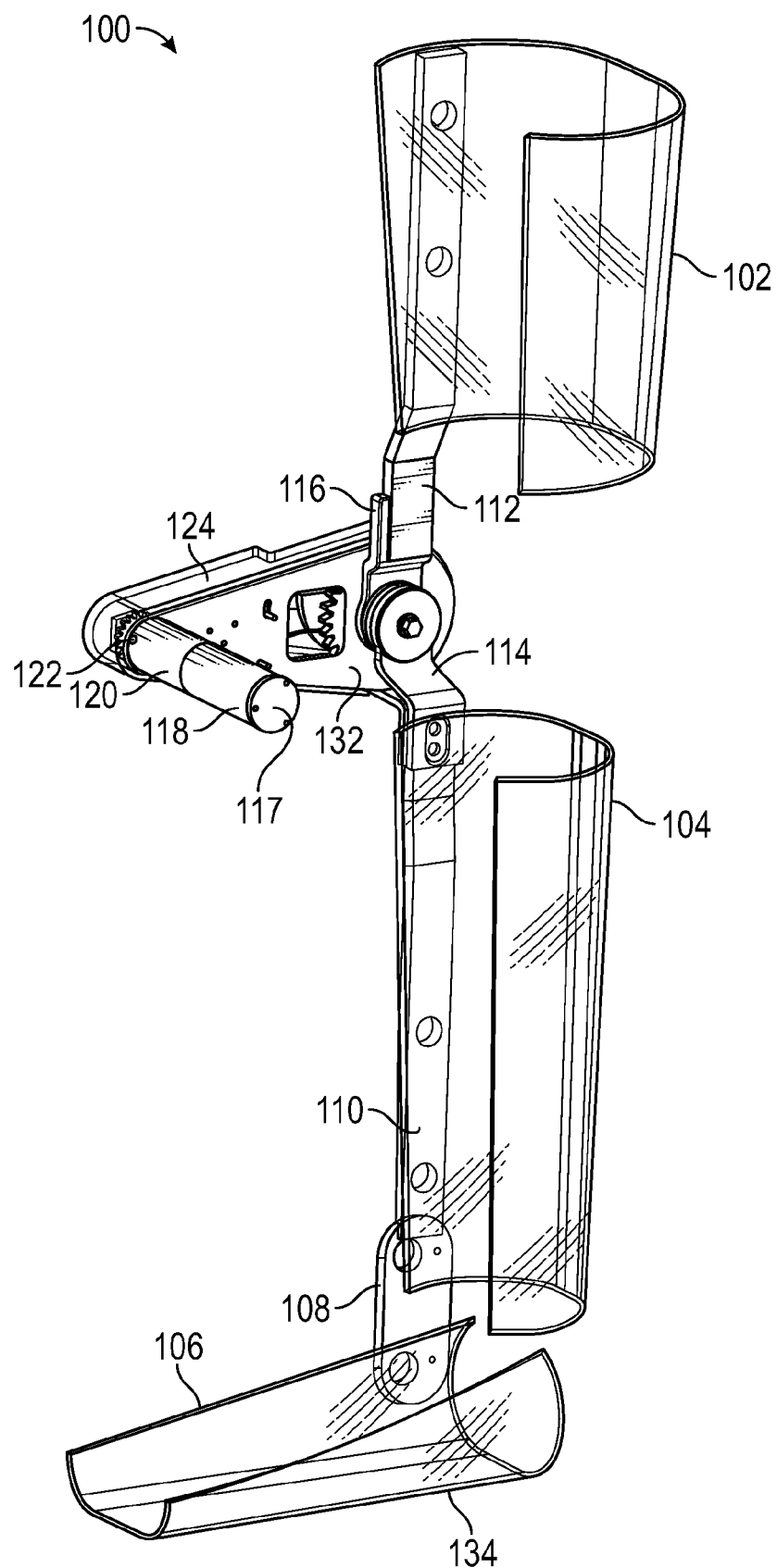
FIG. 3 is a medial-anterior view of the system of FIG. 2.
Figure 4:
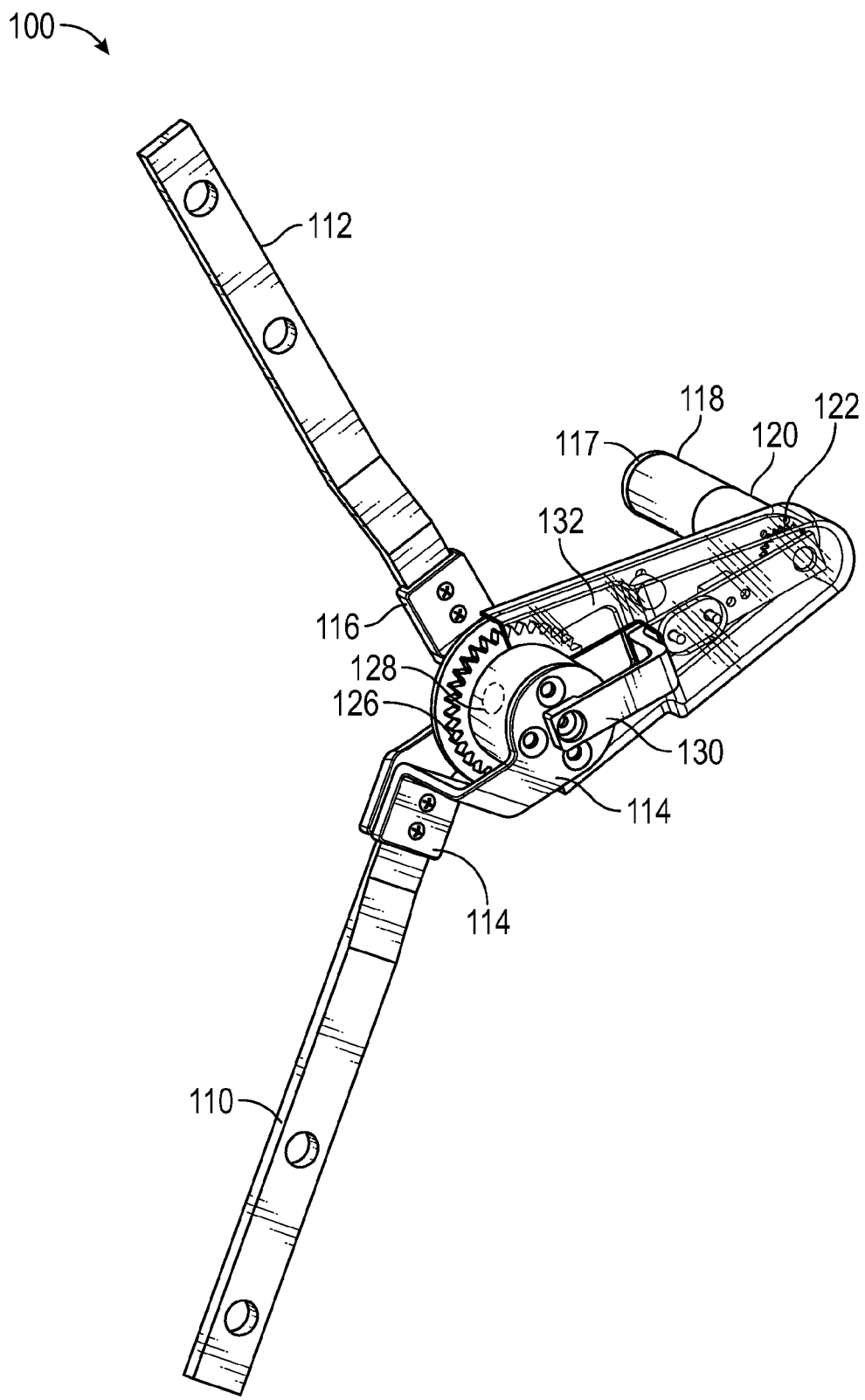
FIG. 4 is a lateral-posterior view of the modular powered knee portion of FIG. 2.
Figure 5:
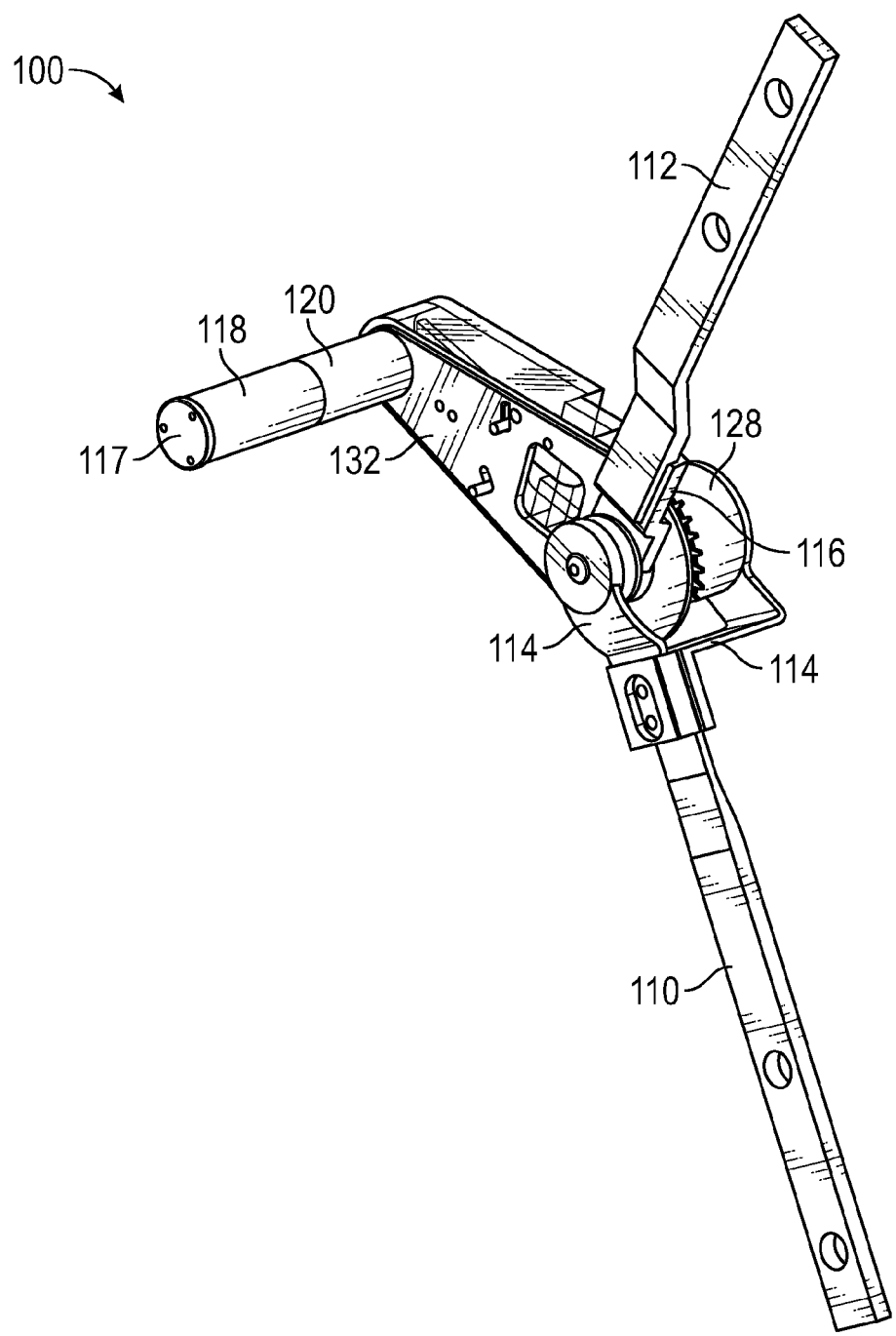
FIG. 5 is a medial-posterior view of the modular powered knee portion of FIG. 2.

As discussed in the Background, there is a need for more effective interventions which can preserve and/or augment strength on a continuous basis for those with crouch gait from cerebral palsy (CP). The primary design focus of modern wearable robotic devices has been on restoring lost function due to paralysis, e.g., from spinal cord injury or stroke, to assist with load carriage, and enhance normal walking efficiency. Transfer of such wearable technologies to pediatric populations has been problematic. Challenges also exist for designing an exoskeleton specifically to treat crouch gait. The conditions that accompany or contribute to crouch, such as spasticity, contracture, instability, poor motor control, and muscle weakness, make the effects and efficacy of introducing motorized assistance unclear in this population.

Disclosed herein are embodiments of new powered devices and associated methods that can assist and augment a wearer's leg posture and strength while walking, and can be effective for rehabilitation of crouch gait in children with CP. Disclosed powered assist devices can be modular such that they can be attached to existing orthotic devices, such as knee-ankle-foot orthotics (KAFOs). Some disclosed device can optionally incorporate surface electrical stimulation (e.g., for functional muscle stimulation and/or electric nerve blocks) and/or accommodate the replacement of the powered motor assistance with a passive spring and/or damper at the knee.

Disclosed powered assist devices can provide powered assistance to knee extension during stance and/or swing phases of gait, helping a patient to more fully extend their leg during key points of their gait while allowing the user to retain volitional muscular control over their gait. Because the devices provide torque that is complimentary to the user's volitionally generated muscle output at the knee, the devices can help to improve the user's walking posture and leg strength over time, training the patient to improve their own gait. Accordingly, the powered devices can serve as a long term treatment and rehabilitation strategy to alleviate persistent knee flexion arising from crouch gait in children with CP. In addition to the knee, other embodiments may apply the same principles at the ankle and/or hip joint, either in combination or in isolation.

While pronounced knee flexion is the hallmark symptom of crouch gait in CP, the musculoskeletal system is a complex linkage with muscles spanning or influencing motion at multiple joints; thus, virtually all lower extremity muscles can induce accelerations at the ankle, knee, and hip and therefore have an impact on the flexed posture observed in this population. The capacity of hip and knee extensor muscles to extend the limb is reduced in a crouched posture while the flexion accelerations induced by gravity are increased. The result is persistent activity of extensors throughout stance phase and transference of responsibility for forward progression to more proximal muscle groups. The disclosed technology can dynamically change the posture during walking and enhance the patient's muscles' ability to extend the limbs.

In addition, targeted strength training of knee extensors can increase knee extension during walking, particularly in the absence of hamstring spasticity. The disclosed powered assist devices can similarly provide targeted strength training of knee extensors along with dynamic extension assistance at the knee and thereby strengthen the muscles while reducing excessive knee flexion and facilitating more normal, appropriate knee extensor activity. When worn for an extended period of time, disclosed devices can have therapeutic benefits in terms of muscle strengthening and improved motor coordination, and can ultimately eliminate the need to wear the powered assistance device.

Exemplary Powered Gait Assistance Devices and Systems

The varying postures and physical deformities present in children with CP, combined with the heterogeneous causes of crouch gait, create a need for versatile, adjustable, and adjustable assistance devices, having human-machine interfaces that can be customized to each individual. Some disclosed powered gait assistance devices can be used with existing leg orthotics, such as knee-ankle-foot orthoses (KAFOs) for example. Conventional KAFOs can comprise custom molded shells for the foot, shank, and/or thigh segments connected by rigid uprights mounted along the side of the leg (see, e.g., FIG. 1). KAFOs can employ joint mechanisms in parallel with anatomical joint centers to allow (or control) segment motion, but typically do not include any powered assistance.

To generate additional assistive torque at the knee joint, some disclosed devices can comprise a powered motor that is coupled via a power transmission to a pivot joint that is positioned adjacent to the patient's knee (e.g., the pivot joint can be part of a KAFO or coupled to the knee joint of a KAFO). The motor and transmission can be positioned in various locations and the transmission can take various configurations, such as a chain drive, cable drive, right-angle drive, or direct drive, for example. The motor and transmission are desirably light weight, low-profile, and capable of providing a sufficient level of torque assistance to the patient. Of course the torque output, and therefore the size and weight, of the device that is sufficient depends on the size and pathology of each particular patient. In other embodiments, torque can be generated by a non-motorized device, such as a spring or spring system. Embodiments disclosed herein that comprise a motor-based torque application may alternatively be constructed using non-motor torque applicators, such as spring and damper mechanisms, at the like.

Internal knee extensor moment output scales with the degree of crouch and body mass, but rarely exceeds and is often much less than 50 Nm for children with mild to moderate crouch. As such, in powered gait assistance systems for such patients, peak torque output need not be very high, which can help reduce the size and power consumption of the device and increase compatibility of the patient's daily life activities. For example, in some embodiments, the powered device can be configured to provide about one third of the internal demand on knee extensors for patients with mild-moderate crouch (e.g., up to about 17 Nm of torque assistance). To provide such levels of torque at the knee joint, a transmission system can be utilized to increase a lower level of torque output from the motor, allowing for smaller motors. However, using a transmission to increase torque output can result in reduced angular speed capabilities. Further, in some exemplary embodiments, the motor-transmission system can achieve a no-load angular velocity similar to peak angular velocity during swing phase knee extension, which can exceed 300 degrees per second.

In some embodiments, the sensors and controller can estimate the internal joint moment applied at the knee (i.e., the volitional muscle effort exerted by the user across the knee joint) and provide assistance based on that effort. In some methods, the assistance may be adjusted using a feedback controller which tracks volitional knee extensor moment (effort) and provides assistance as a percentage of instantaneous internal knee moment, thereby encouraging volitional muscle use while also providing knee extension assistance.

In some methods, the assistive torque may be adjusted in anticipation of an upcoming shortfall in volitional knee extension effort. The target for this approach can be to proactively adjust the posture of the limb so that the user's own muscles are able to create more torque around the joint. In this manner, the powered system can facilitate and/or encourage the user to activate their own muscles, producing the desired training effect. After repeated exposure to these adjustments, the resulting increased muscle activation can be adopted as a new walking strategy, enabling the assistance required to be slowly decreased over time. Examples of this can include anticipatory knee extension assistance during late swing to enable improved extension torque during loading response, and anticipatory knee extension during mid-stance to facilitate passive knee flexion and active ankle plantarflexion during push-off. Other anticipatory adjustments can be applied as well.

In some methods, the torque provided across the joint may act to resist the intended joint motion to provide targeted muscle training during walking. The target for this approach can be to proactively elicit excessive volitional muscle activity in an effort to provide gait-phase specific strength training during walking. In this manner, the system can facilitate enhanced activation of the user's own muscles beyond the typical activation during walking. After repeated exposure to this resistance, and the accompanying increased muscle activation, the resulting elevated muscle activation can be adopted as a new walking strategy without the device. Examples of this can include applying a flexor torque at the knee joint to resist knee extension during late swing, and/or applying a plantarflexor torque at the ankle during early swing to resist ankle dorsiflexion.

Figure 19:
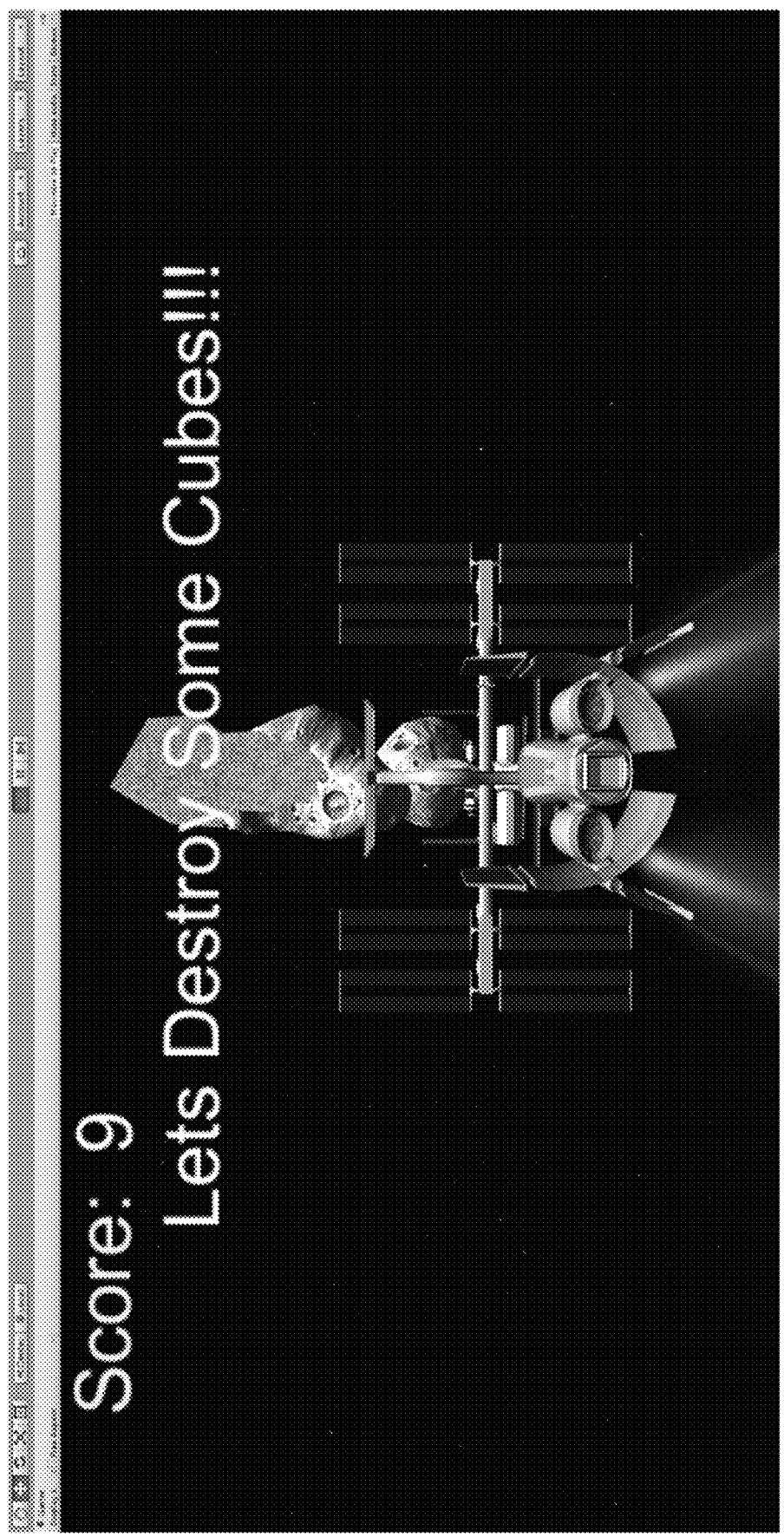
FIGS. 19 and 20 are screen shots from an exemplary computer game usable to help train patients using disclosed powered gait assistance systems.
Figure 20:
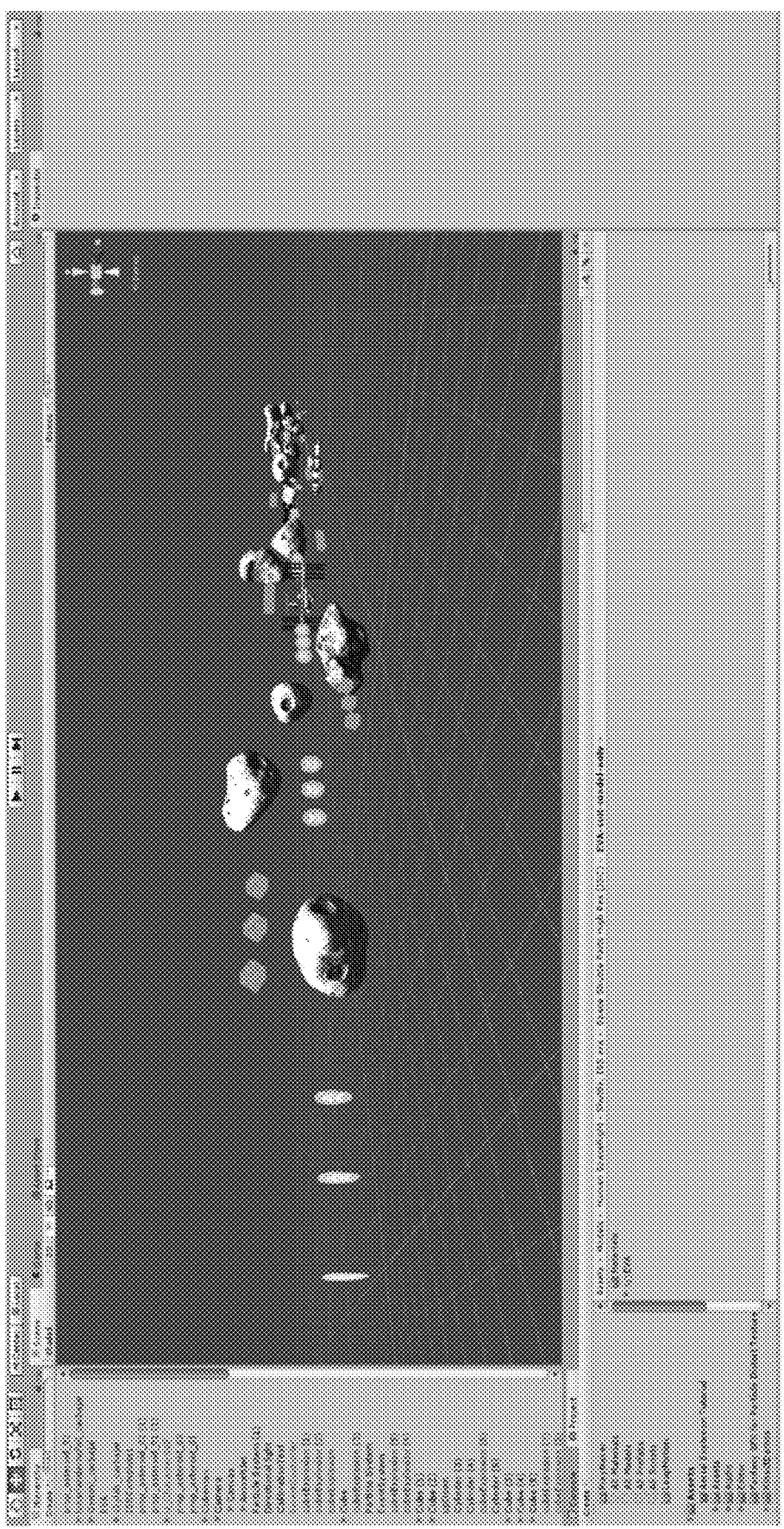

In some other embodiments, real-time biofeedback can be incorporated into the control strategy such that the user is made aware of their limb posture during walking for the purpose of eliciting greater volitional effort of knee extension. The biofeedback can be provided in the form of electro-tactile, vibro-tactile, auditory, and/or visual feedback, among others. Incorporating biofeedback with the exoskeleton provides a mechanism for which to incentivize the training of improved gait postures with the aid of robotic assistance. One possible embodiment of this incentive is to utilize the feedback to create a video (or audio) based game (i.e., gamification), as illustrated in FIGS. 18-20, to encourage training and reward retention of the improved gait posture or walking strategy.

FIG. 1 illustrates an exemplary powered gait assistance system 10 that was constructed and tested (as discussed below) with a child having crouch gait from CP. The system 10 includes orthotic braces 12 of an existing KAFO and modular powered torque assist system 14 including rigid members 16 that couple to the KAFO braces 12 at the thigh and shank and a motor-transmission assembly 18. As shown in the inset of FIG. 1, the motor-transmission assembly 18 includes an encoder 21, electrical motor 22, gear box 24, transmission comprising a chain 26 and sprockets 28 and 30, chain tensioner 32, chain guard 34, and torque sensor 36. The system 10 can also include a ground contact sensor 38 mounted below the foot to detect when the patient's foot is in contact with the ground and when the leg is in the swing phase.

FIGS. 2-5 show various views a modular system 100 similar to the system 10 in FIG. 1. The system 100 includes thigh brace 102, shank brace 104, foot brace 106, ankle linkage 108, rigid shank member 110, rigid thigh member 112, rigid torque members 114, 116 coupling the members 110, 112 to the powered knee mechanism, encoder 117, motor 118, gear box 120, sprockets 122, 126 coupled via chain transmission 124, torque sensor 128, rigid transmission frame members 130, 132, and ground contact sensor 134. The motor 118 can comprise a back-drivable 24 V, 90 W brushless motor with a 3-stage, for example. The gear box 120 can comprise an 89:1 reduction planetary gear head, for example. The encoder 117 can comprise an embedded quadrature encoder, for example. The chain sprocket transmission can provide a 3.5:1 speed reduction, for example, and can transmit torque from the inline shaft of the motor to the knee center of rotation. Other speed reductions ratios can be provided in other embodiments based on the motor and the patient's needs. The maximum rated output torque of the tested assembly in one embodiment is approximately 16.1 Nm with a 3.82 amp maximum continuous current draw. The torque sensor 128 can be mounted on the drive shaft at the knee and provide a feedback signal indicating the currently applied assistive torque. The powered gait assistance assembly can be modular such that it can be attached to the lateral uprights on the thigh and shank, and/or other portions of existing KAFOs.

To facilitate both powered assistance and the allowance of unrestricted knee motion during various phases of the gait cycle, the motor can be mounted anterior and superior to the knee joint, as shown in the exemplary systems 10 and 100, for example. The motor-transmission assembly can be attached to both the lower (shank) and the upper (thigh) uprights of a KAFO such that the torque output causes the lower upright to pivot relative to the upper upright, assisting the patient's knee motion. Each upright can connect to and disconnect from a custom molded shell or other portion of the KAFO via quick release attachment mechanisms to facilitate simple and speedy removal and attachment even after the KAFO has been donned by the user.

In some embodiments, an adjustable ankle joint mechanism, such as an adjustable dynamic response (ADR) ankle joint device, can be mounted on the lateral upright and can connect the foot and shank components of the system. The adjustable ankle joint mechanism can be located adjacent the angle linkage 108 in the system 100, for example. The adjustable ankle joint mechanism can be freed to allow unencumbered ankle motion, locked to restrict motion, or adjusted to provide dynamic assistance. The system can also include a force sensitive sensor 134, such as force sensitive resistor (FSR) mounted on the foot portion 106 of the device to detect and provide information regarding foot-ground contact. The foot portion 106 of the system can include a foot plate that goes under the patient's foot and is worn inside the shoe. The force sensitive sensor 134 can be coupled to the foot plate and located under the patient's foot to detect when the patient's weight is applied down on the foot plate, indicating when the foot is on the ground and the leg is in the stance phase of the gait.

The system 100 can also include a controller (not shown) comprising circuitry that provides power and signal conditioning for sensors (e.g., torque sensors, knee angle sensors, ground contact sensors, etc.) as well as feedback control of the motors. The controller can be positioned anywhere, such as mounted near the motor, on the side of the leg, on the upper body, or in a remote device that is coupled to the rest of the system via wires or wireless means. The controller can include or be coupled to servocontrollers that enable closed loop current control of the device motors (e.g., to control torque application at the knee) and knee joint position feedback based on encoder quadrature. Sensor signals can be input into a feedback control system implemented in an onboard computer/processor for real-time, autonomous control. The system can powered by an onboard batteries, for example.

FIGS. 13-17 show additional alternative embodiments of powered gait assistance devices, as described in more detail below.

Exemplary Controllers and Algorithms

Rule-based hierarchical control, as implemented in a finite state machine (FSM), can be deployed for control any of the disclosed systems to help assist and/or restore walking ability. Splitting the gait cycle into discrete states based on detected gait events provides enhanced consistency and robustness to an inherently variable process and allows implementation of lower level controllers within each state. In the exemplary FSM shown in FIG. 7, the gait cycle is divided into three discrete phases: stance 202, early swing 206, and late swing 210. FSM thresholds can be selected based on various criteria, such as data obtained from evaluated children with mild-moderate crouch, and can be verified and adjusted (if necessary) during initial walking sessions for each particular patient. As shown at 204, 212 and 214, the foot plate sensor can be used to govern the transition between stance and swing states based on detected foot ground contact. As shown at 208 and 216, knee angle position and velocity (e.g., computed as first derivative) can be used to detect transition between early and late swing phases. A proportional-integral-derivative (PID) control scheme can be used, for example, to achieve the desired torque output at the knee within each state. The PID error value can be computed as the difference between the measured and desired torque. In some embodiments, the PID gains can be adjusted prior to a patient donning the device, so that torque output reaches a stable response with minimal chatter and latency. For example, in an exemplary system, when the set-point is zero, as in early swing, the PID controller can compensate for the inherent friction of the motor-transmission assembly, allowing for the knee joint to be freely articulated (e.g., effectively frictionless).

Figure 8:
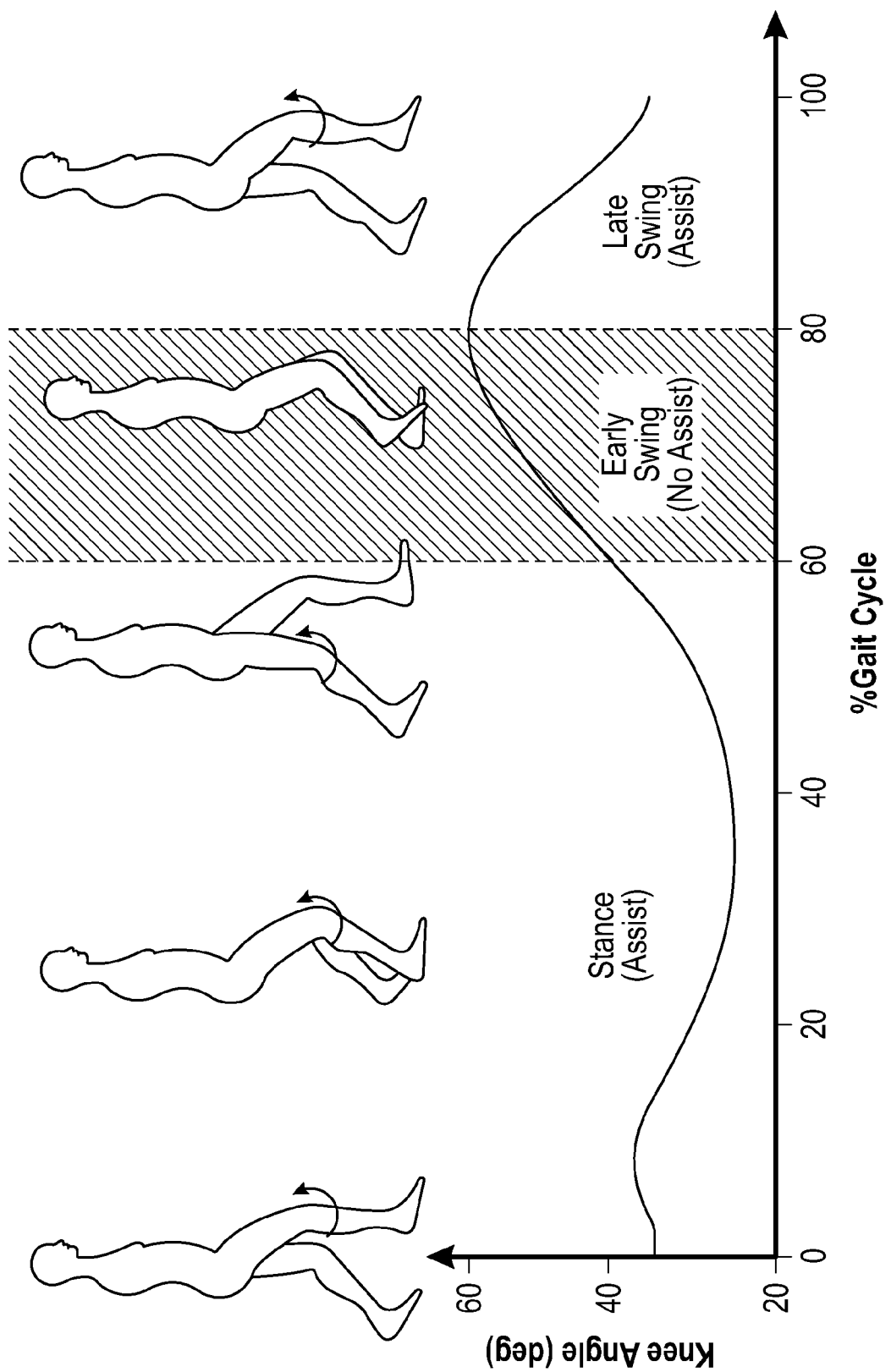
FIG. 8 is a diagram illustrating the gait cycle and exemplary portions of the gait cycle when knee extensor assistance can be provided and not provided.

Various control strategies can be implemented to provide knee extension assistance at different intervals within the gait cycle. For example, as shown in FIG. 8, the powered device can provide extension torque at the knee during stance phase to assist body weight support and during the late-swing phase to assist knee extension for foot placement. At the same time, the control strategy can provide for a frictionless (e.g., near zero torque applied) period during early swing to facilitate knee flexion for toe-clearance.

Figure 9:
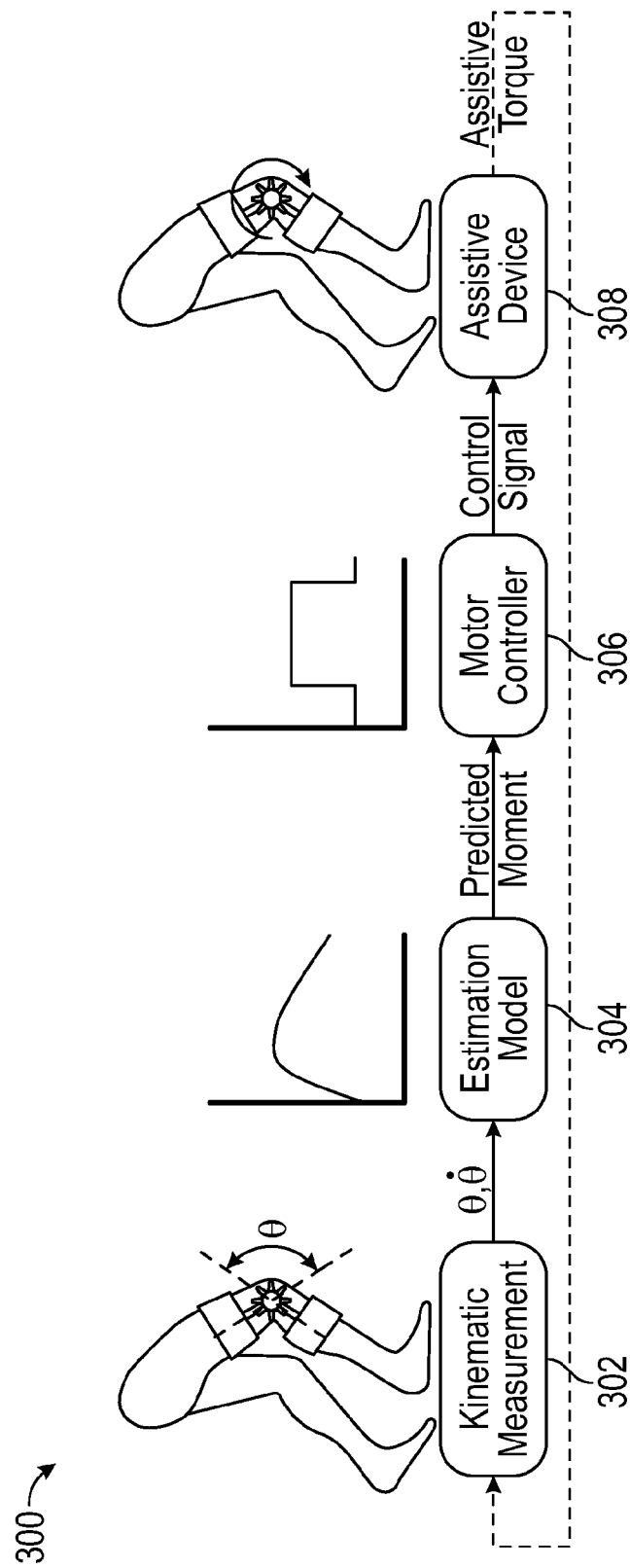
FIG. 9 is a schematic illustrating an exemplary control architecture for a gait assistance system.

FIG. 9 is a flow diagram illustrating an exemplary control architecture 300 for the disclosed gait assistance devices. At 302, kinematic measurements are made (e.g., knee joint angles, other joint angles). The kinematic measurements 302 are fed into an estimation model 304 that outputs a predicted moment profile for the patient over the gait cycle. The predicted moment profile can be generated based on the kinematic measurements 302 along with various other input data, such as patent size, weight, muscle strength, crouch severity, etc. The predicted moment profile can then be fed to a motor controller 306 that converts the predicted moment profile into an electrical control signal appropriate for the particular motor/transmission system being used (e.g., the assistive device 308). The assistive device 308 then provides an assistive torque profile over the gait cycle based on the control signal and optionally based on real-time sensory feedback during the gait cycle. The control architecture 300 can cycle continuously over the gait cycle to provide real-time adaptive control for the powered system.

Exemplary Device Testing and Evaluation

Figure 7:
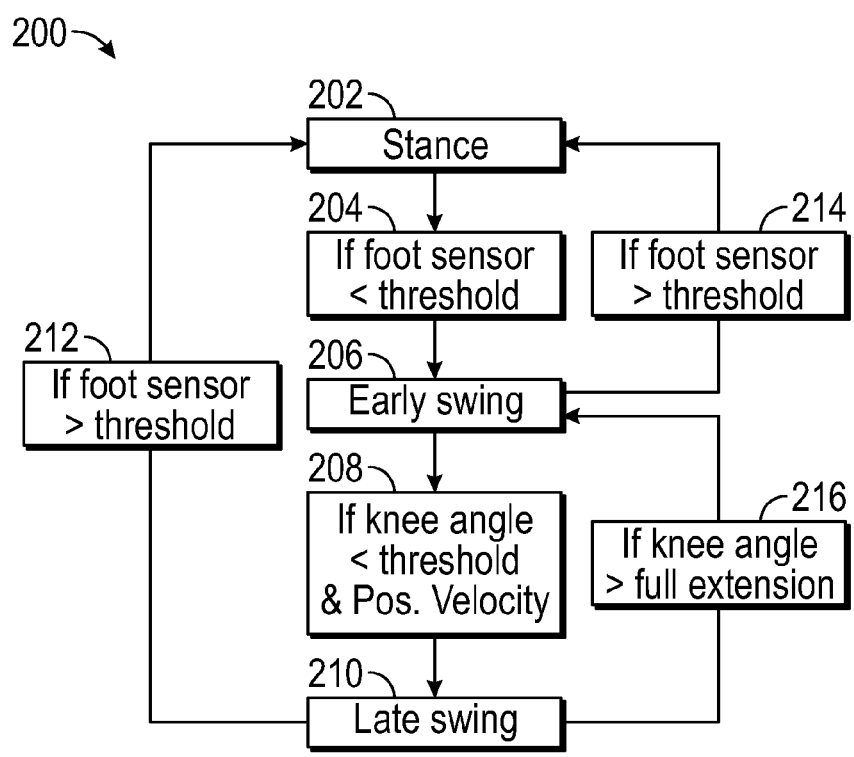
FIG. 7 is a diagram of an exemplary finite state machine used to specify desired knee extensor assistance at different phases of the gait cycle.

To validate the functional performance and efficacy of the exemplary gait assistance system 10 shown in FIG. 1, implementing the disclosed control strategy illustrated in FIGS. 7 and 8, one male participant diagnosed with crouch gait from CP was recruited and evaluated. He was classified level II on the gross motor function classification system (GMFCS) and was able to walk for at least 30 feet without assistance. At the time of data collection, he was six years old, height of 118 cm, and weight of 20.0 kg.

The participant completed five sessions of testing and evaluation. The first session included a clinical assessment of lower limb strength and spasticity, over-ground gait assessment of his baseline gait condition while wearing prescribed AFOs on each leg, and casting for fabrication of custom orthotic braces. The initial session was followed by three practice sessions, during which the participant walked with the powered gait assistance system over-ground and on a treadmill, and a final session for data collection. When using the powered gait assistance system, the participant was instructed to walk in a manner similar to their normal walking habits.

During the practice sessions, the system torque output was adjusted upwards from 1 Nm at 0.5 Nm increments. Final values of 3.5 Nm for stance phase and 2.625 Nm (75% of the stance value) for swing were established based on participant preference and visual feedback of participant comfort and walking stability. Total walking time in the powered gait assistance system was 18 minutes across the four sessions. Frequent short breaks were given to reduce fatigue and maintain participant attention and focus on the walking task. Total walking time does not include experimental setup, device tuning and calibration, or walking in control conditions (i.e., without powered assistance). The motor controller also incorporated safety measures that limited the maximum torque output and prevented knee hyperextension.

The fifth session was for experimental data collection with the gait assistance system under two conditions: a free knee joint (no motor assist) and the assistive mode with extensor torque set at 3.5 Nm for stance phase and 2.625 Nm (75% of the stance value) for swing (FIG. 8). The purpose of these conditions was to assess the effect of the passive braces and the motorized assembly on gait separately. The ankle joint was set for free rotation in both conditions. The participant completed three successful overground walking bouts along a 5.5 m pathway in each mode. Kinematic data were collected at 100 Hz using 10 motion capture cameras and a custom marker set. Specifically, three markers were placed on the foot, clusters comprised of four non-collinear markers on the shank and thigh segments, four markers on the pelvis, and three on the trunk. Markers were also placed on the medial and lateral aspects of the ankle and knee joints. Three markers were placed on each shank and thigh segment of the orthotic brace. Muscle activity was collected bilaterally from rectus femoris, vastus lateralis, semitendinosus, and medial gastrocnemius using a wireless EMG system recorded at 1000 Hz. EMG data were band-pass filtered at 15-380 Hz, full-wave rectified, and low-pass filtered at 7 Hz to create a linear envelope. Lower-extremity joint angles were computed from marker trajectories. Experimental data were time normalized to each gait cycle and averaged across the gait cycles for each walking condition.

Performance Validation

Figure 10:
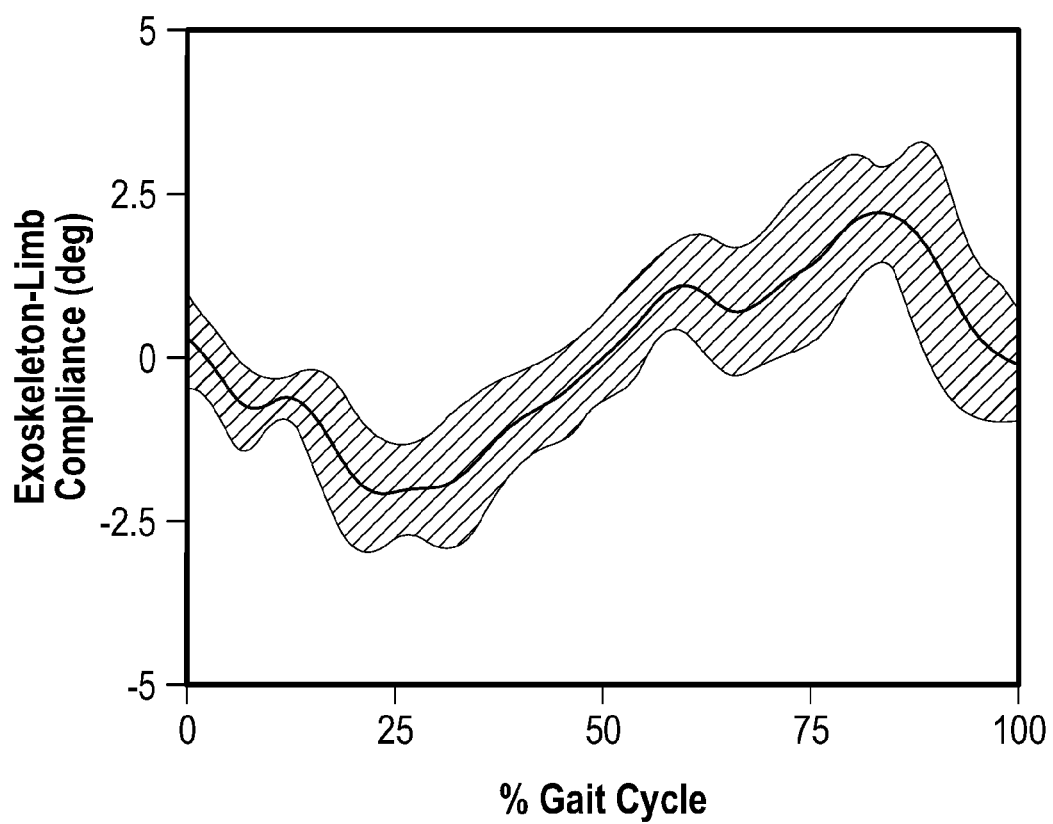
FIG. 10 is a graph showing mean angular compliance between a patient and an exemplary gait assistance system throughout the gait cycle.
Figure 11A:
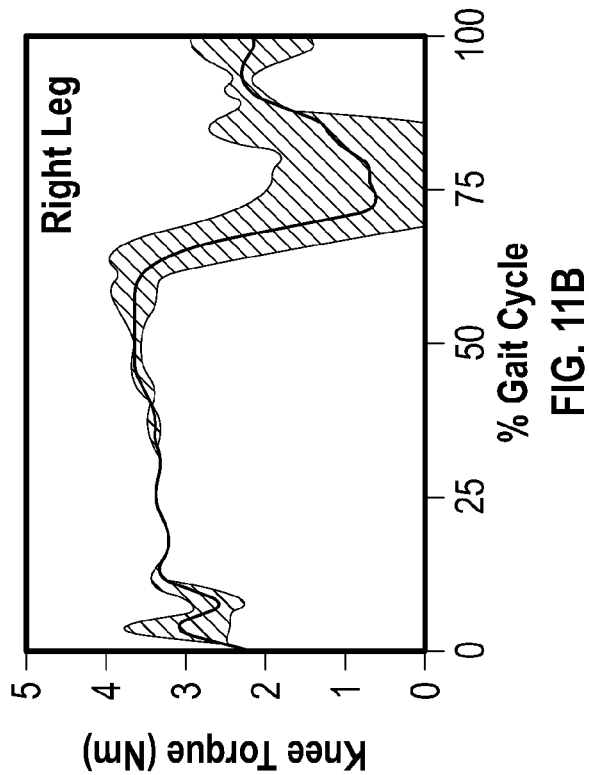
FIGS. 11A and 11B show mean knee extensor torques applied by an exemplary gait assistance system across the gait cycle, as measured by an onboard torque sensor at the knee.
Figure 11B:
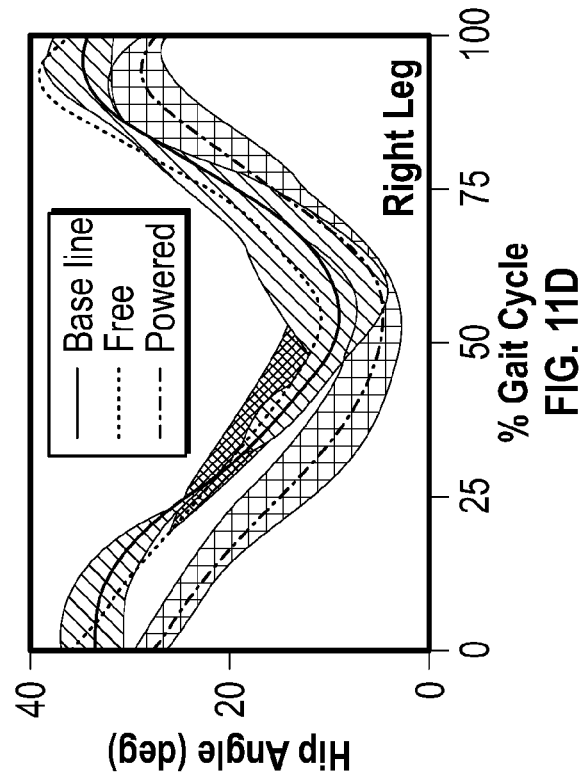
Figure 11C:
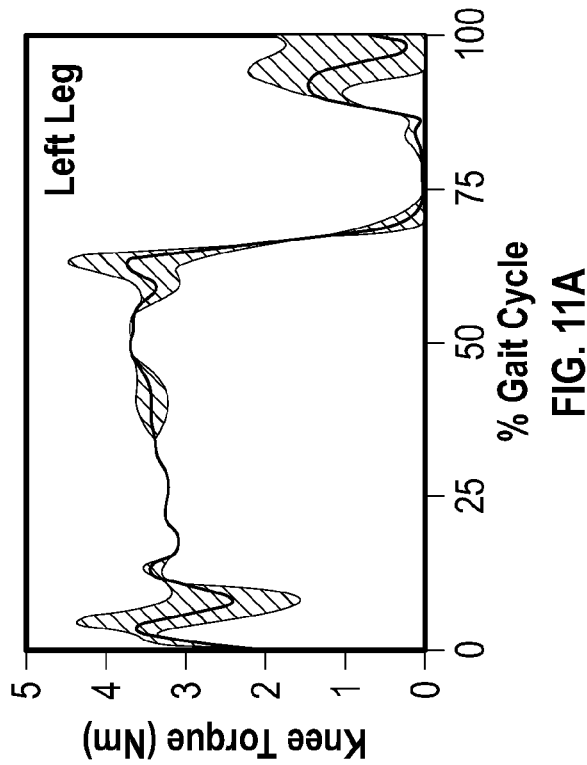
FIGS. 11C-11H show mean sagittal plane hip, knee, and ankle joint angles across the gait cycle during baseline, free, and powered system conditions. Shaded regions represent plus-minus one standard deviation from the mean.
Figure 11D:
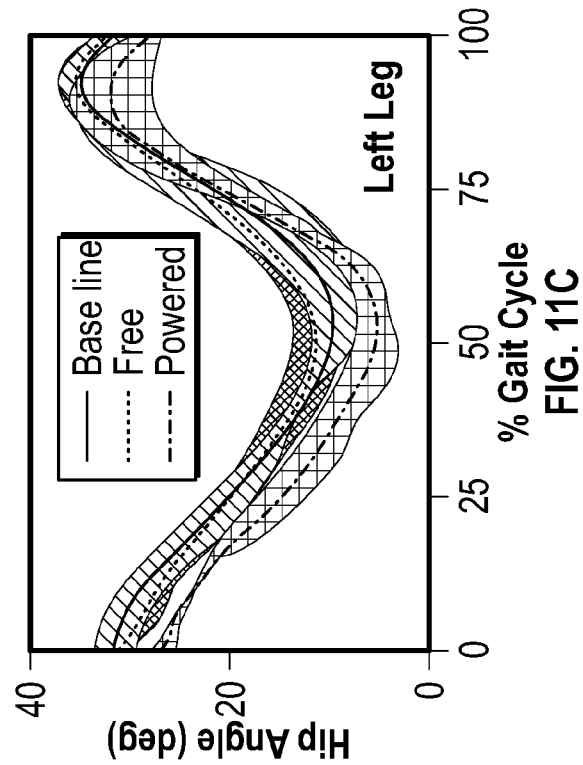
Figure 11E:
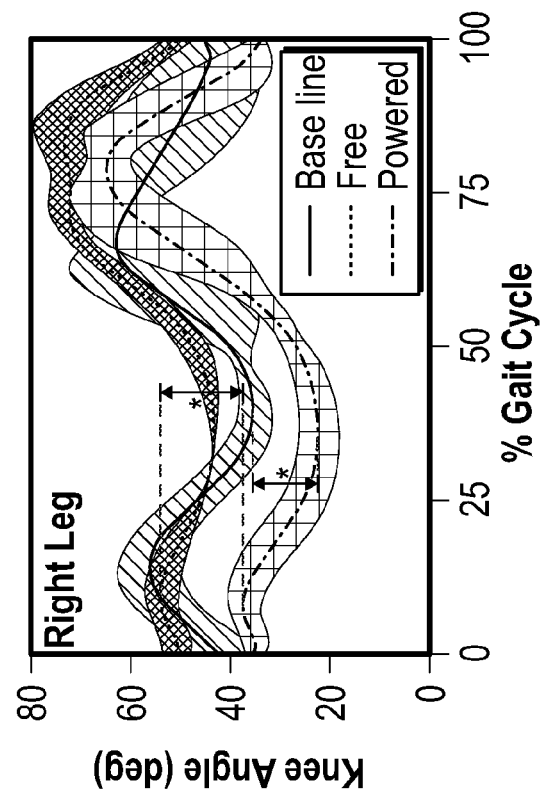
Figure 11F:
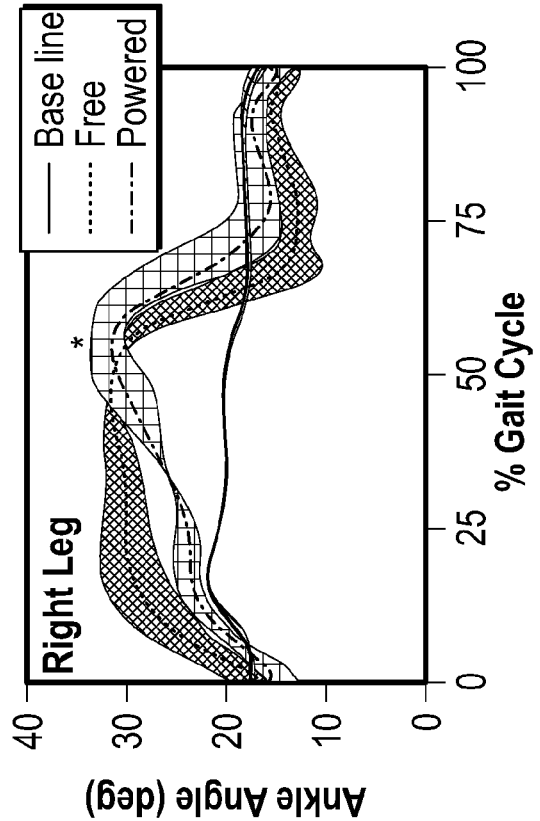
Figure 11G:
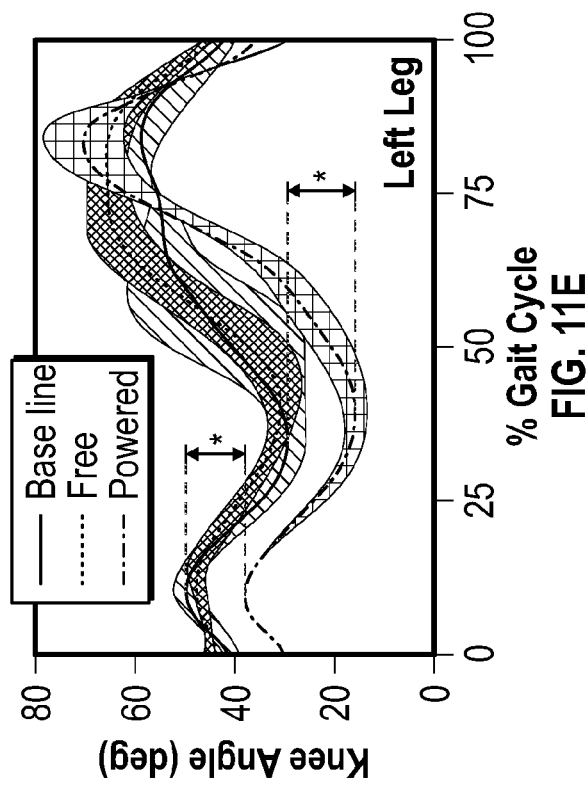
Figure 11H:
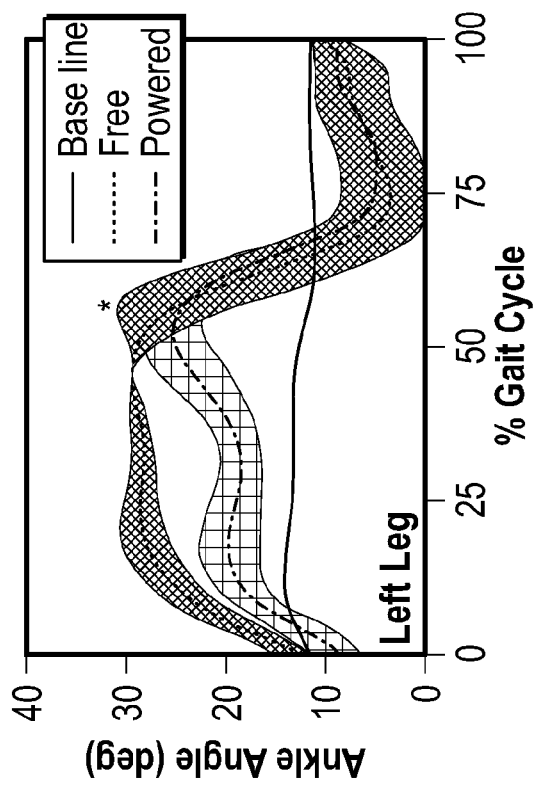
Figure 12A:
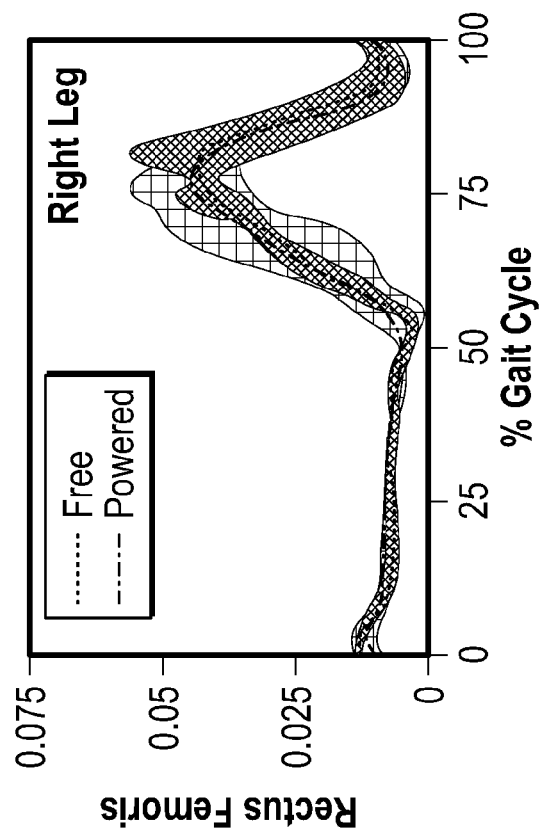
Figure 12B:
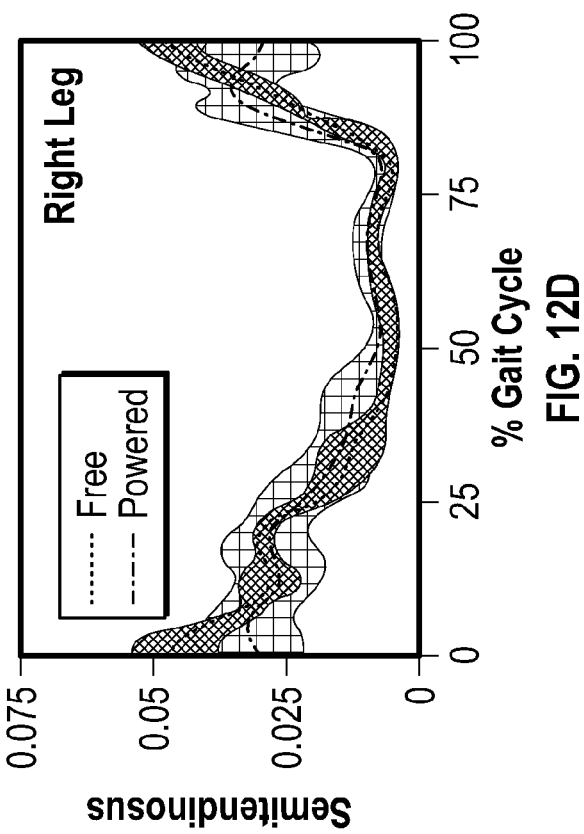
Figure 12C:
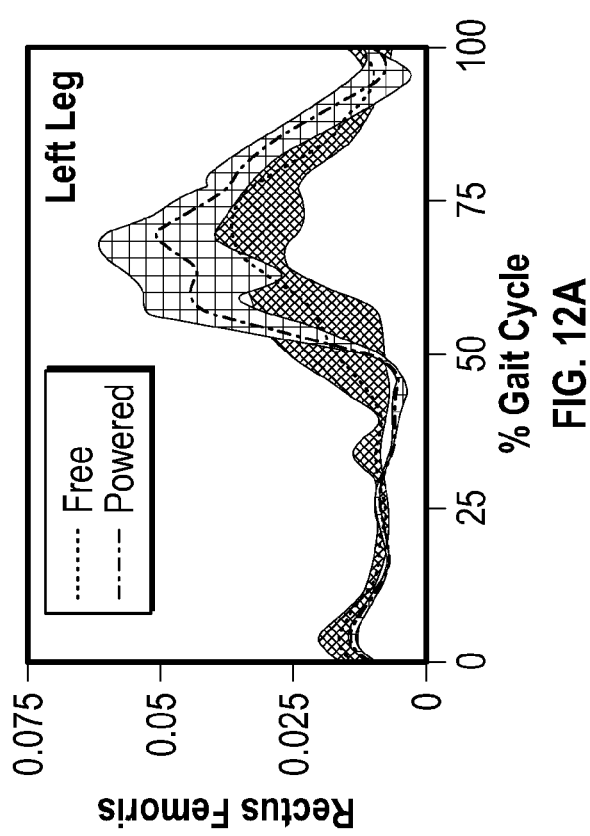
Figure 12D:
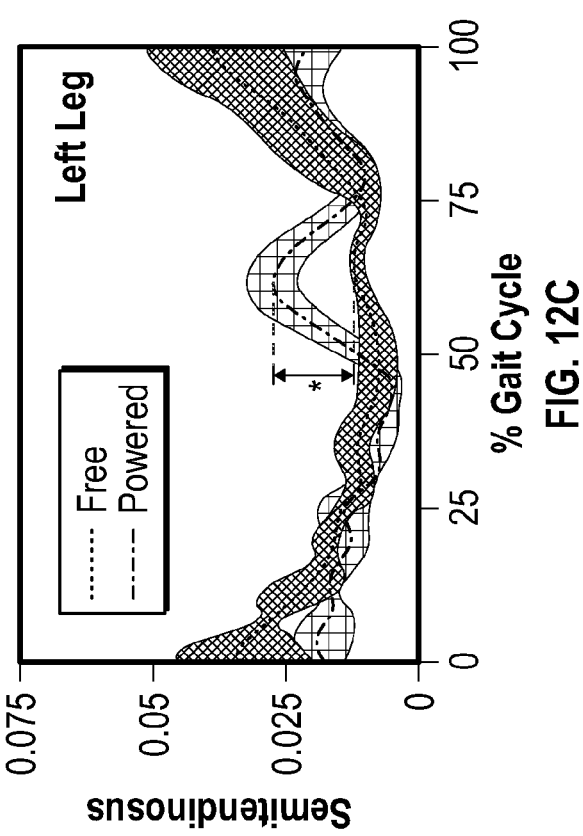

The latency of the exemplary gait assistance system 10 was measured by attaching the uprights to a solid extruded aluminum frame, creating an isometric condition under which timing of torque application could be quantified. The on-off and off-on latency was measured as the time between when the controller triggered the transition and when torque measured by the onboard sensor reached the target value. The average latency, across 10 trials, was 53±8 ms for activation and 57±7 ms for deactivation. The compliance between the brace and limb was evaluated by comparing sagittal plane knee joint angle computed from the system markers with the biological knee angle computed from markers placed directly on the skin, as shown in FIG. 10. The difference in knee angle was not significant ($p>0.99$) indicating minimal motion between the patient's body and system. As shown in FIGS. 11A and 11B, the torque provided by the powered system was consistent with the design specifications. Swing phase assistance was provided only after volitional knee extension began. Swing phase knee extension was delayed in the left leg compared to the right leg, which resulted in a reduced interval during which swing extension assistance could be applied to the left limb prior to heel-strike.

Joint Kinematics and Spatiotemporal Measures

The experimental biomechanics data obtained from over-ground walking were screened to ensure that only complete gait cycles free from adverse events (e.g., toe-drag) were included in the subsequent analyses. The total number of analyzed gait cycles for each condition, along with other data obtained, is shown in the table in FIG. 6.

As illustrated in FIGS. 11C-11H, to assess the effects of motorized extension assistance on the participant's gait, kinematics (joint angles) and spatiotemporal parameters were calculated under three conditions: shod+AFO (baseline), walking with the powered system with a free knee joint (free), and walking with assistance from the powered system (powered). There was a significant increase in total knee range of motion (ROM) and knee extension during stance phase when walking with the powered system compared to the free knee and baseline conditions (as shown in FIG. 6). Compared to baseline, the powered system increased peak knee extension during stance by 18.1° and 11.5° in the right and left leg, respectively. Maximum knee flexion during stance was decreased in the powered condition by similar levels (18.6° and 11.9°) compared to baseline. There was no significant difference in the hip angle between the baseline, free knee, and powered conditions. However, peak ankle dorsiflexion was increased significantly for both the free knee and powered conditions due to the free ankle joint compared to the rigid AFO at baseline. Yet, there was no significant difference in knee extension during stance or knee ROM between the baseline and free conditions. There were no significant differences in step length or step width between walking conditions. Cadence was significantly reduced in both the free knee and powered conditions compared to baseline.

Muscle Activity

As shown in FIGS. 12A-12H, walking with the powered system affected EMG activity of several muscles compared to walking with the brace with a free knee joint. There was elevated activity during late stance phase in both rectus femoris and semitendinosus in the powered condition. Post-hoc tests showed a significant increase in peak semitendinosus linear envelope during late stance ($p<0.001$). Importantly, the tested powered gait assistance system did not have a large effect on the vastus lateralis activity, which maintained similar levels during late-swing and stance phases when assistance was provided. Likewise, no differences in medial gastrocnemius EMG were observed between the free knee and powered conditions.

Discussion

The exemplary powered systems and control methods described herein can significantly help with ambulation, especially as a treatment of crouch gait in children with CP. The testing and evaluation described above examined the effects of relatively straightforward knee extension assistance during stance and late-swing phase. The analysis shows that the exemplary FSM control strategy activated and deactivated the assistance during walking with latencies of similar duration to those of biological processes (e.g., muscle contractions), and therefore are well-suited for adequate human-machine interaction.

The evaluation also assessed the level of relative motion that was permitted between the patient's limbs and the exemplary device when assistive torque is applied. The data indicate that the as-tested powered gait assistance system and implementation strategy suitably mitigated this issue as no significant motion of the system was observed relative to the underlying limb at the knee joint in the patient. Owing to the patient's weight (20.0 kg), the target torque levels were small but sufficient to demonstrate the functional capacity of the device to elicit the desired outcomes (e.g., increased knee extension during stance). The torque set-point during each assistive phase was held constant at 3.5 Nm for stance and 2.6 Nm for swing, respectively. Even though the torque was constant for each state, the resulting kinematic profile maintained relatively normal waveforms, including continuous knee extension for foot placement and an early stance loading response. In other embodiments, more sophisticated control methods can be utilized, to even more effectively inject additional energy into the gait cycle to alleviate crouch.

The tested device significantly altered lower extremity kinematics and reduced the amount of crouch compared to the baseline condition. As a result, the subject walked in a more extended, upright posture, and showed significant increases in maximum knee extension during stance phase in both the left and right legs. The improvement in maximum knee extension (12-19°) was similar to the range of long-term improvement reported from invasive surgical treatment (10-20°). Peak stance phase knee flexion was also significantly reduced in both legs when walking with the powered system. The participant displayed baseline asymmetry with slightly less crouch during stance in the left leg. The testing results illustrate that the assistive torque, set to the same value in both legs, had a larger effect on stance posture in the more affected limb. Other embodiments can employ alternative methods for delivery of assistive torque, such as by varying levels of assistance between limbs and/or adjusting the amount of torque applied within each phase in real-time.

The overall knee ROM for the entire gait cycle was significantly increased during walking with the powered system, resulting in a trajectory that was closer to that of normal waking. While there were gains in knee extension during stance, an increase in knee flexion during swing phase was also observed with both the powered system and the free knee condition.

The increased knee ROM provided by the powered system can mitigate the kinematic benefit of extension assistance provided by the motor. A more flexed knee during swing increases the late swing extension requirement as the limb must articulate through a larger ROM. In the testing results, the transition from swing phase flexion to swing phase extension was delayed in the left leg compared to the right, limiting the time available to provide swing phase assistance from the powered system. Peak swing knee extension velocity in the left leg was approximately 350°/sec, resulting in motor shaft velocity of 18,160 revolutions per minute (RPM), which exceeded the no load speed of the motor (16,300 RPM or 314°/sec) and therefore limited the ability to provide extension assistance in this phase (FIGS. 11A and 11B). Swing phase knee extension velocities in the right leg were less than 300°/sec. In other embodiments, a higher power motor with a lower gear reduction can be deployed.

The tested torque set-points were also relatively small and selected according to patient preference and visual observation of walking stability. The applied torque levels were gradually increased during testing over the three practice sessions. Still, the participant walked with reduced cadence while using the powered system compared to his baseline gait, a somewhat expected finding given the novelty of the task that may be improved with additional time for accommodation to the system. Considering the limited time the participant walked with the powered system, continued use would likely result in increasing comfort levels, the opportunity to increase the assistance, and further kinematic improvements.

Differences in EMG were observed during walking evaluation with the tested powered system. In the left leg, elevated hip and knee flexor activity at the end of stance phase and in early swing (50-75% of the gait cycle) was observed. The knee extensor torque provided by the motor at the end of stance may have triggered this antagonistic flexion response. No differences were observed in knee extensor activity during stance or swing phase extension assistance in either leg. At the end of the stance phase in the left leg, vastus lateralis activity ceased earlier when using the powered system compared to the free knee. This pattern of activity more closely resembles that of normal walking, and illustrates the application of the disclosed technology for long term use of the disclosed assistance devices to help facilitate elimination of the persistent extensor activity during stance phase of crouch.

Robotic assistance during walking can be employed in neurologically intact populations without diminishing muscle activity, and can actually increase muscle activity. The testing results described herein show that certain patients, such as children with crouch gait from CP, do not significantly reduce their knee extensor activity when walking with powered extension assistance from a powered gait assistance system. For example, it was observed that the test participant did not simply allow the motors to take over control of knee extension responsibilities and that kinematic improvements were observed. The disclosed powered assistance devices can maintain and increase the user's volitional muscle activity over time, making them suitable as a rehabilitation tool.

Another challenge for long-term use of powered gait assistance systems, especially in children, is growth of the patient over time. Accordingly, the disclosed technology can be modular, adjustable in size and power, and can comprise or be used with orthotic devices that do not require custom molding to be individually adaptable. This can have the added benefit of reduced cost as well as longer-term adaptability.

Another advantage of the disclosed technology as a therapeutic intervention is that the implemented control strategy can be tuned to optimize the assistance for each individual, and can be changed over time as the patient changes. The modular design allows optional integration of additional modes of assistance, such as passive support at the ankle and surface electrical stimulation.

Alternative Embodiments of Powered Gait Assistance Systems

The systems illustrated in FIGS. 1-5 are representative of a wide variety of possible system in which the disclosed technology can be implemented. In alternative embodiments, the system can utilize different types of motors, transmissions, controllers, sensors, quick-connect mechanisms, etc. For example, the motors can comprise electrical motors, pneumatic or hydraulic actuators, artificial muscles, etc. The transmissions can comprise direct drives, belt drives, chain drives, Bowden cables, geared drives, etc. The systems can be employed on one leg of a patient only, or on both legs. The technology can also be employed analogously on other joints, such as the ankle or hip joints. The motor and transmission system can also be positioned in different locations, such as to the lateral side of the leg, below the anterior aspect of the knee, at the hips or torso, etc. In some embodiments, it is desirable to reduce the lateral width of the device, such as when the patient uses a wheel chair, walker, or crutch. In other embodiments, it may be desirable to locate motor components far from the knee, such as at the hip or thigh, and use a chain, belt or cable type transmission to transfer torque to the knee joint. The device-limb interface can also have various structures, such as rigid thermoplastic orthotic braces, compliant restraints such as cloth, webbing, synthetic skin materials, or other interfaces. In some embodiments, the system controller can communicate wirelessly with other remote devices (e.g., via radio, cellular networks, WiFi, Bluetooth, NFC, etc.). For example, the controller may communicate with a cloud based databases or remotes computing systems to exchange information, data logging, remote control and adjustment of system settings, firmware/software updates, etc.

Figure 13:
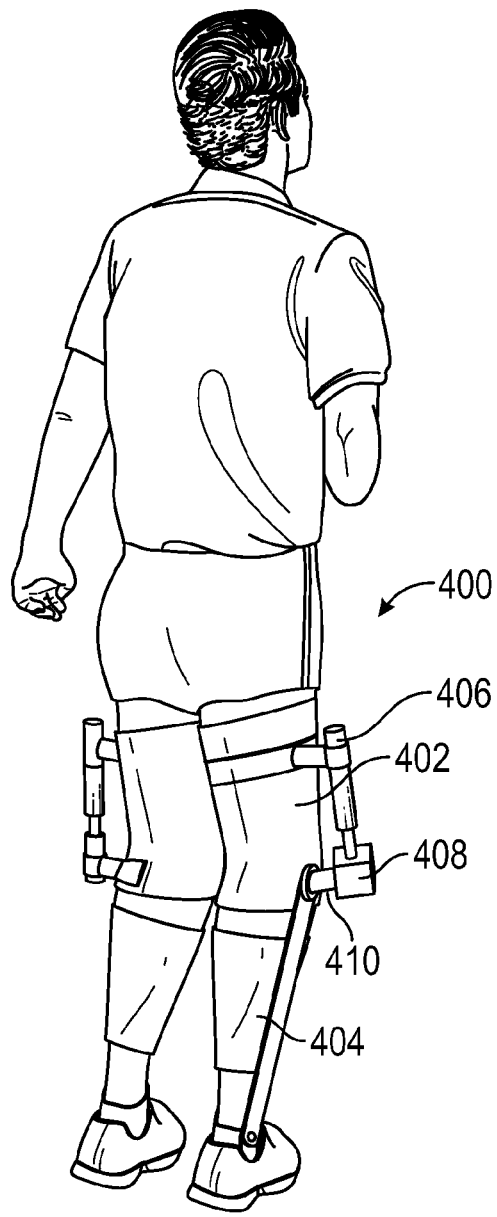
FIG. 13 shows an exemplary gait assistance system comprising motors oriented along lateral aspects of the thighs and coupled to knee joints via right-angle drives.

FIG. 13 shows an exemplary powered gait assistance system 400 that includes a motor 406 mounted along the lateral aspect of the patient's thigh brace 402. The motor is coupled to the knee joint 410 via a right-angle drive 408 to apply assistive torque to pivot the shank 404 relative to the thigh. In this system, there is less structure anterior to the knee, and the mass of the motor is shift upward closer to the hip joint, which can reduce the added burden on the hip muscles caused by the system. The system 400 also obviates the need for cables or chains to transmit power.

Figure 14:
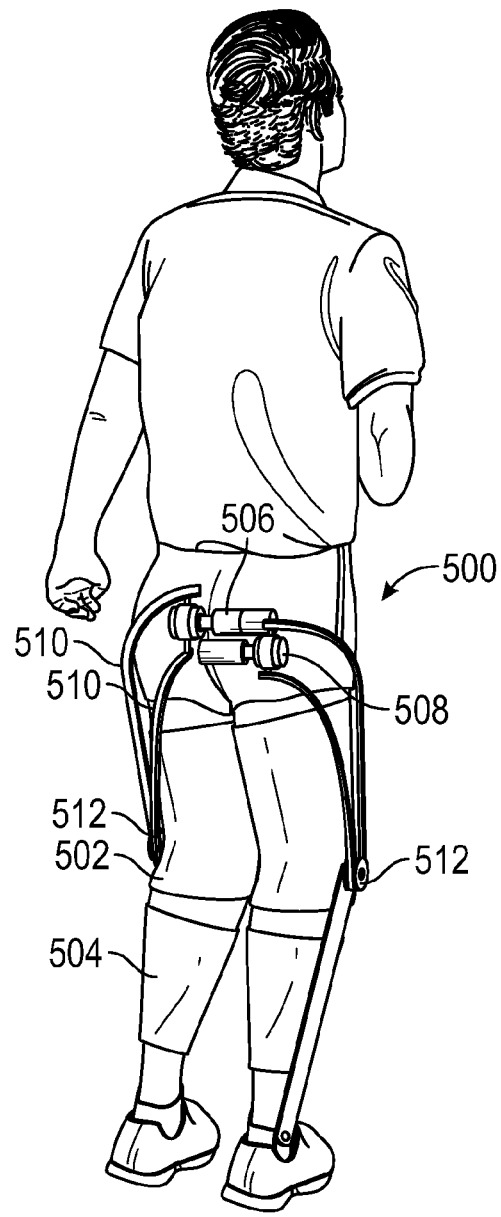
FIG. 14 shows an exemplary gait assistance system comprising torso mounted cable-drive motors coupled to knee joints via tensioned cables.

FIG. 14 shows an exemplary powered gait assistance system 500 that includes torso mounted cable-drive motors 506. The motors 506 include cable drives 508 that apply tension to cables 510 running down the lateral aspect of the thighs to knee pulleys 512, which use the cable tension to apply torque to the knee joints. The system 500 minimizes the structural impedance around the legs, allowing less obstruction of gait motion between the braces 502 and 504. The cables 510 can be protected by being routed through tubes, for example.

Figure 15:
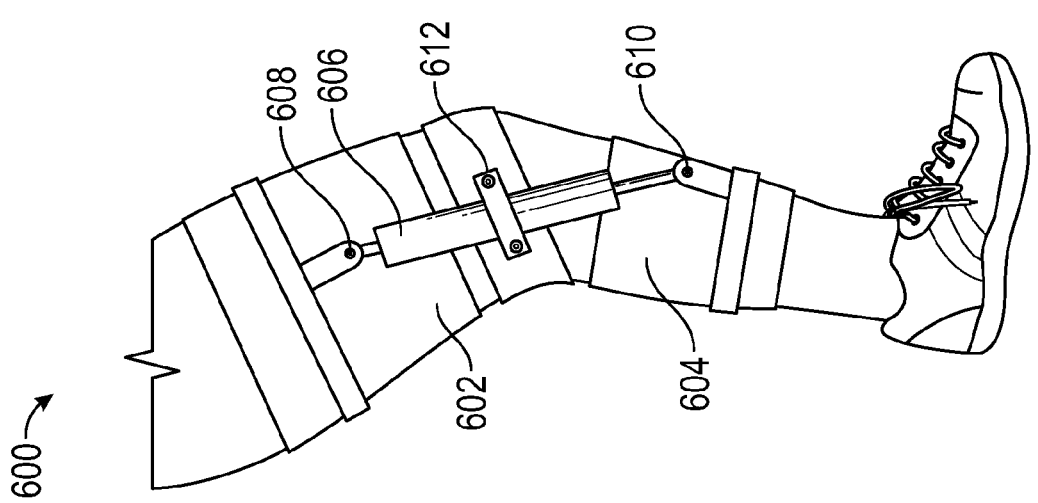
FIG. 15 shows an exemplary gait assistance system comprising a linear actuator coupled between a thigh brace and a shank brace to provide torque at the knee joint.

FIG. 15 shows an exemplary powered gait assistance system 600 that includes a linear actuator 606 that has a first end 608 coupled to a thigh brace 602 and a second end 610 coupled to a shank brace 604. Linear extension and contraction of the actuator 606 causes torque application about the knee joint 612. The system 600 allows there to be minimal structures around the knee joint.

Figure 16:
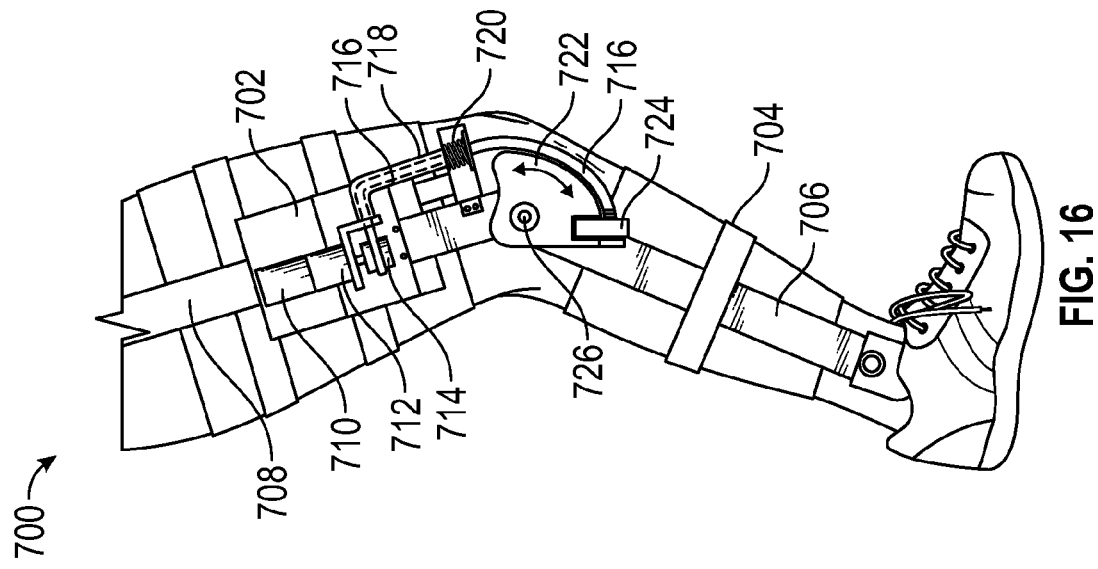
FIG. 16 shows an exemplary gait assistance system comprising a thigh mounted motor that drives a cable coupled to a shank portion along an arcuate path to provide torque about the knee joint.

FIG. 16 shows an exemplary powered gait assistance system 700 that includes a thigh brace 702 coupled to a shank brace 704 via rigid uprights 706, 708 and a pivot joint 726, with a motor 710 and gearbox 712 mounted along the thigh. The motor turns a cable driver 714 that pulls and pushes a cable 716 that follows an arcuate path through a cable guide 718 around the knee joint 726 to a connection point on a lower member 722 fixed relative to the shank upright 706. The cable drive 714 pushes and pulls the cable to cause the member 722 to pivot the shank about the joint 726. A load cell 716 can be mounted at the end of the cable to measure the applied force. A spring or other biasing member 720 can be included in the upper portion and coupled to the cable to help bias the cable, such as to avoid kinking/crimping of the cable and maintain tension in the cable. The system 700 can provide a greater range of motion over which the assistive torque can be applied, such as over knee angle range from 90 degrees to 270 degrees.

Figure 17:
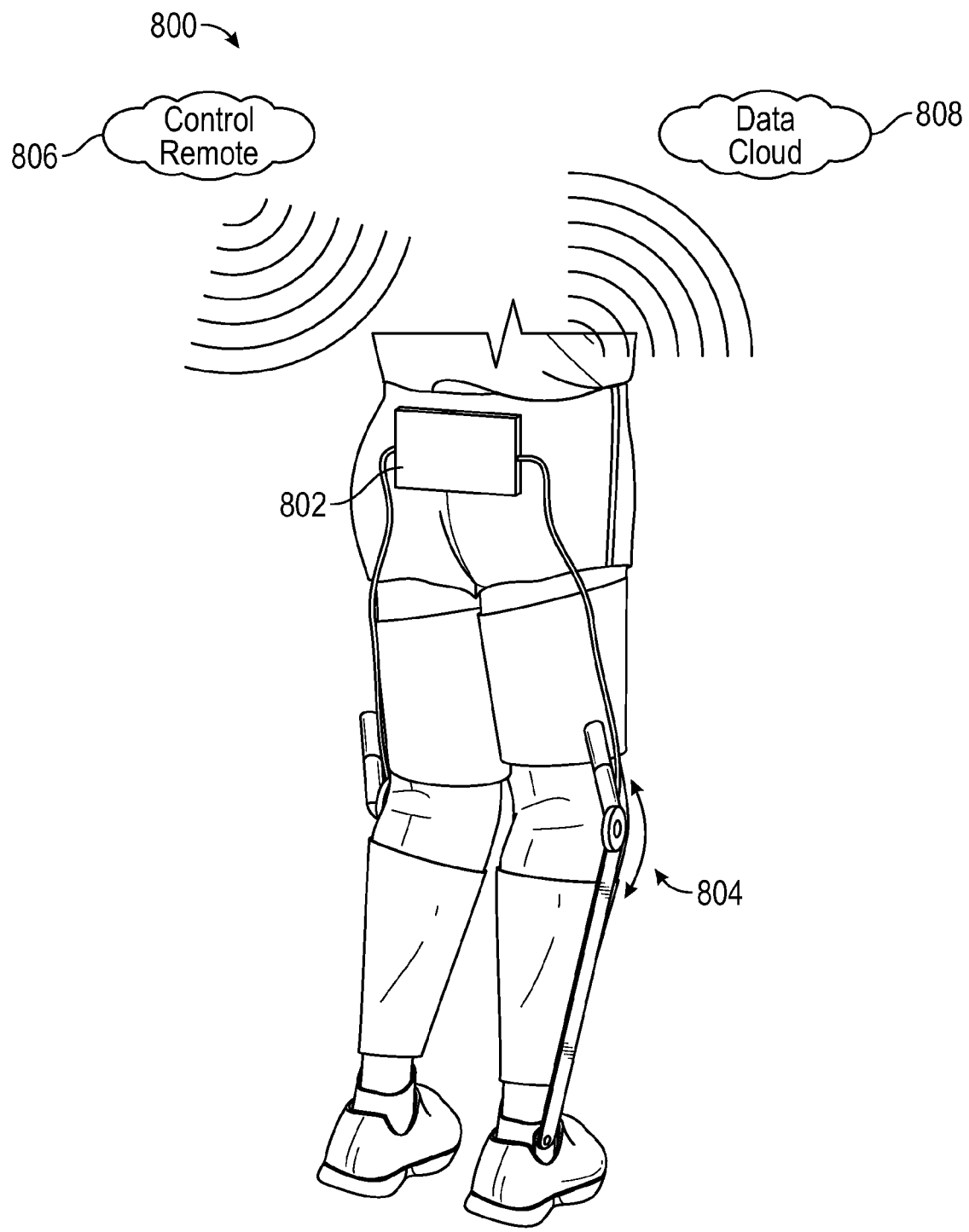
FIG. 17 shows an exemplary gait assistance system comprising a body mounted system controller that is wirelessly coupled to a remote control system and/or to a cloud based computing environment/data base.

FIG. 17 shows an exemplary powered gait assistance system 800 that includes a system controller 802 configured to control the powered gait assistance system 804 (e.g., any of the disclosed arrangements) wherein the controller 802 is wirelessly coupled to one or more remote systems, such a removed computing or control system 806 and/or a cloud based computing environment or database 808. The controller 802 can include an onboard microcontroller that adjusts torque assistance of the mechanism 804 based on wireless communications with remote systems, such as with researches or clinicians, and can send back data regarding the performance, compliance, etc. of the system. The controller 802 can also communicate wirelessly with the motors and/or sensors of the system 804. The controller 802 can optionally also include memory/data storage to store data until a later time when it can be communicated or used in processing steps.

The controller may optionally include a mobile application user interface to adjust the type, timing, and level of assistance, to provide user-interaction for bio-feedback based games for training, and to report user performance while using the exoskeleton system.

Figure 18A:
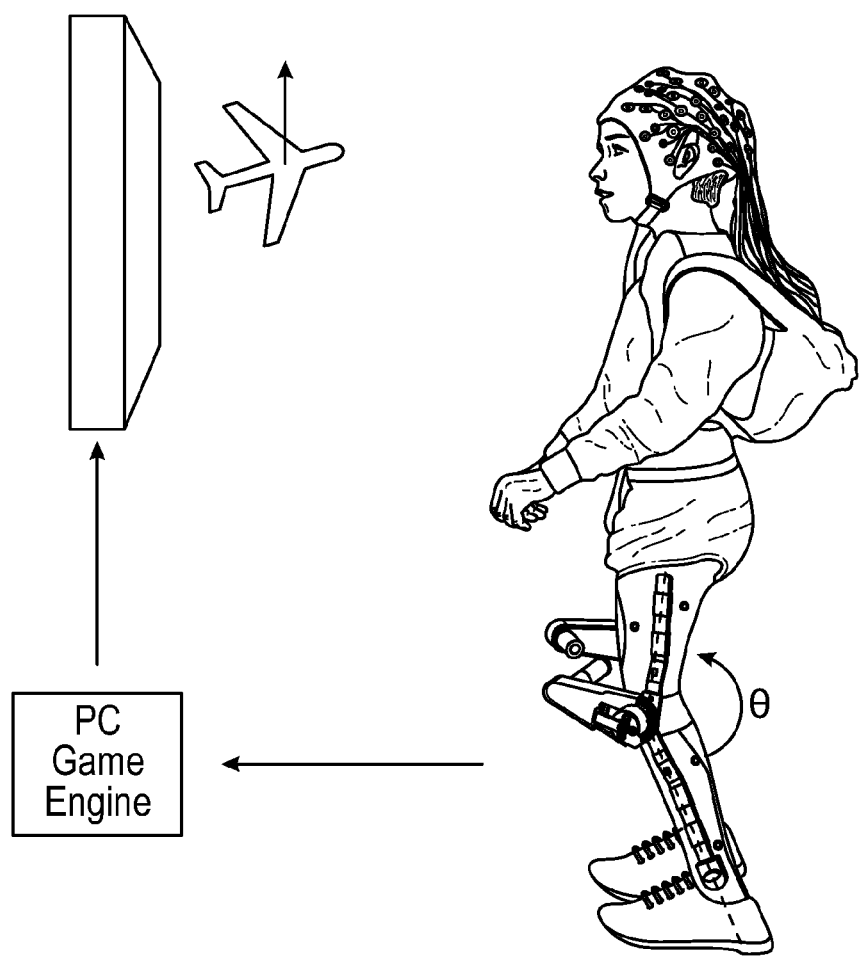
FIGS. 18A and 18B illustrate an exemplary computer game system that can be used to help train patients using disclosed powered gait assistance systems.
Figure 18B:
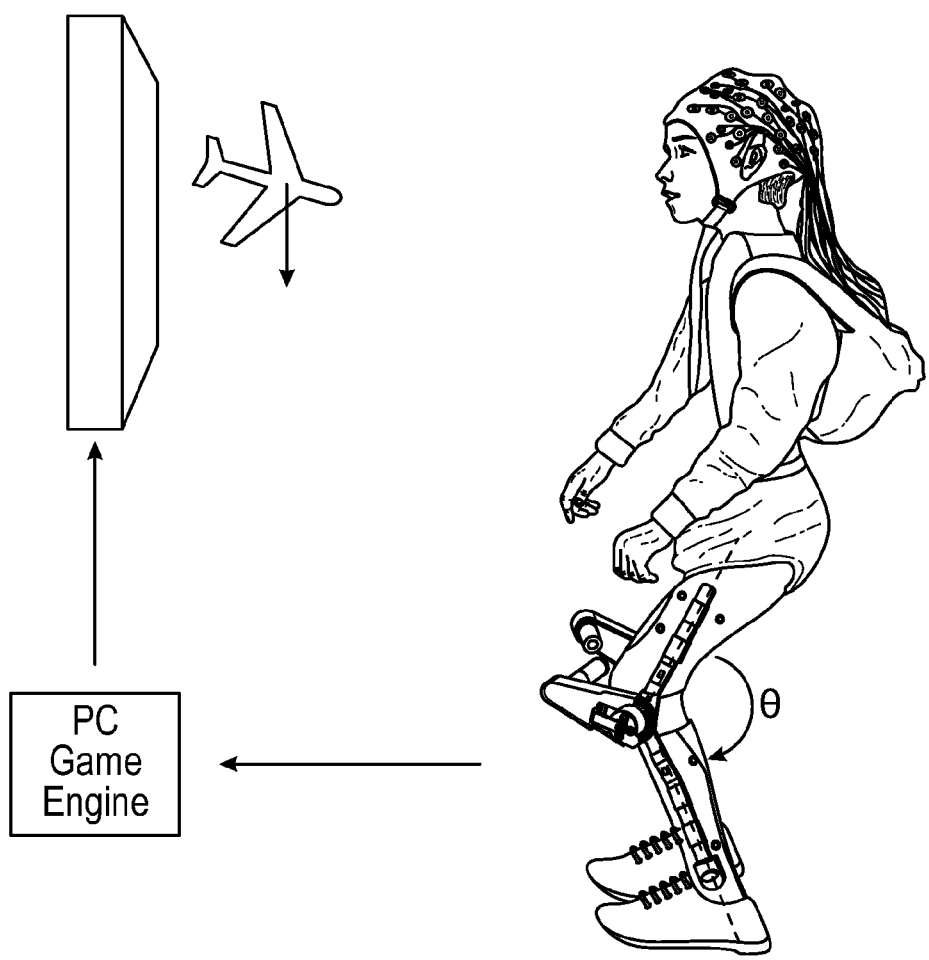

FIGS. 18A and 18B show a computer based game system that can be used to help train a patient wearing one of the disclosed powered gait assistance systems. The game can show images that encourage the patient to bend and extend at the knees in a desired sequence, such as to control an avatar or other object in the game. This can help the patient, especially a child, perform the desired amount of repetitions and foster improved training results, while making the training fun and rewarding.

Gaming mechanisms and immersive/non-immersive forms of virtual reality are showing promising results and rapidly gaining traction for neuro-rehabilitation. The powered gait assistance systems may optionally be used as a peripheral device in this emerging field of neurorehabilitation gaming Disclosed gait assistance systems can be capable of collecting and transmitting real-time measurements capturing user movement and effort, and as a result, can be integrated as a game controller for a custom application for exercise targeting knee extension and flexion in children with crouch gait from CP. Proper game control resulting in successful completion of repetitive exercises provides strengthening and cardiovascular training to the user. In addition, when coupled with a neuroimaging modality such as electroencephalography (EEG), these games allow for analysis of brain activation during task execution, allowing for further optimization of both game development and treatment strategies to maximize neuroplasticity. FIGS. 18A and 18B demonstrate knee movements measured by the worn device being used as input to drive a game engine capable of rendering real-time feedback to the patient using either immersive (head mounted display) or non-immersive virtual reality technologies. The software integration pipeline can utilize commercial game engines to broaden the scope of use of the powered gait assistance devices as a haptic game controller for neurorehabilitation gaming and tele-rehabilitation applications.

For example, FIGS. 19 and 20 show screenshots of an exemplary training game, where squatting at the knees causes a spaceship to move down and extending at the knees causes a spaceship to move up. The patient controls the spaceship to try get the spaceship to move up and down in real time to hit certain objects in the spaceship's flight path, creating a game that the patient can play and enjoy while training.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A powered gait assistance system, comprising:
a first arm and a second arm coupled together to allow relative pivoting between the first and second arms, wherein the first arm is configured to be coupled to an upper leg portion of a patient and the second arm is configured to be coupled to a lower leg portion of the patient such that relative pivoting between the first and second arms is about an axis proximate the patient's native knee pivot axis;
a motor coupled to the first and second arms and operable to apply torque between the first and second arms to urge relative pivoting between the first and second arms;
a torque sensor that measures magnitude of torque applied to the first and second arms;
an angle sensor that measures a relative angular position between the first and second arms;
a foot sensor that measures contact of the patient's foot with a ground surface;
at least one muscle output sensor configured to measure a volitional knee pivoting muscle output; and
a controller programmed to:
determine a stage of a gait cycle a leg of the patient is in based on signals from one or more of the foot sensor, the angle sensor, and the torque sensor;

determine a volitional knee pivoting muscle output via one or more muscle output sensors over the course of the gait cycle; and based on the determined stage of the gait cycle, cause the motor to apply a level of torque between the first and second arms to assist or resist the volitional knee pivoting muscle output during selected stages of the gait cycle, such that the torque applied by the motor improves the patient's leg posture over the gait cycle, wherein the level of torque applied between the first and second arms is based on the volitional knee pivoting muscle output, wherein the level of torque between the first and second arms during at least one stage of the gait cycle assists the volitional knee pivoting muscle output to improve the patient's leg posture, and the level of torque applied to the knee joint during at least one other stage of the gait cycle resists the volitional knee pivoting muscle output to increase the strength of at least one targeted muscle over time.

2. The system of claim 1, wherein the improvement to the patient's posture causes the patient to walk in a more energy efficient manner.

3. The system of claim 1, wherein the torque applied by the motor at selected stages of the gait cycle increases the patient's knee range of motion and reduces crouch during the gait cycle.

4. The system of claim 1, wherein the system allows the patient to produce greater volitional muscle output at the knee joint.

5. The system of claim 1, further comprising a chain or cable transmission system that transfers power from the motor to the first and second arms.

6. The system of claim 1, wherein the system is modular and can be attached to or include a traditional knee-ankle-foot orthotic.

7. The system of claim 1, wherein the system resists patient knee joint extension by applying a flexor torque during a late swing phase of the gait cycle prior to foot touch down.

8. The system of claim 7, wherein the system assists patient knee joint extension during a ground contact phase of the gait cycle prior to toe take off.

9. The system of claim 8, wherein the system provides no assistive torque or resists patient knee joint flexion during an early swing phase of the gait cycle after toe take off.

10. The system of claim 1, wherein the motor is positioned anterior to the patient's knee.

11. The system of claim 1, wherein the motor is positioned lateral to the patient's thigh.

12. The system of claim 1, wherein the motor is positioned on the patient's torso or hips.

13. The system of claim 1, further comprising a transmission system that increases torque output of the motor.

14. The system of claim 1, wherein the controller is programmed to wirelessly communicate with a remote computing system or cloud based communication system.

15. The system of claim 1, wherein the system is adapted for use as a computerized training game controller, wherein the patient can control action in a computerized training game by volitionally flexing and extending at the knees while wearing the system.

16. A method of controlling a powered gait assistance device, comprising:

determining a stage of a gait cycle a leg of a patient utilizing the powered gait assistance device is in based on signals from a ground contact sensor and a knee angle sensor of the powered gait assistance device;

determining a volitional knee pivoting muscle output via one or more muscle output sensors over the course of the gait cycle; and based on the determined stage of the gait cycle, causing the powered gait assistance device to apply a level of torque to a knee joint of the patient to assist or resist the volitional knee pivoting muscle output during selected stages of the gait cycle, such that the torque applied improves the patient's leg posture over the gait cycle, wherein the level of torque applied to the knee joint is based on the volitional knee pivoting muscle output, wherein the level of torque applied to the knee joint during at least one stage of the gait cycle assists the volitional knee pivoting muscle output to improve the patient's leg posture, and the level of torque applied to the knee joint during at least one other stage of the gait cycle resists the volitional knee pivoting muscle output to increase the strength of at least one targeted muscle over time.

17. The method of claim 16, wherein the level of torque causes the volitional knee pivoting muscle output to increase over time.

18. The method of claim 16, wherein causing the powered gait assistance device to apply the level of torque to the knee joint comprises resisting patient knee joint extension by applying a flexor torque during a late swing phase of the gait cycle, prior to foot touch down.

19. The method of claim 17, wherein causing the powered gait assistance device to apply the level of torque to the knee joint comprises assisting patient knee joint extension during a ground contact phase of the gait cycle prior to toe take off.

20. The method of claim 19, wherein causing the powered gait assistance device to apply the level of torque to the knee joint comprises providing no assistive torque or resisting patient knee joint flexion during an early swing phase of the gait cycle after toe take off.

21. The method of claim 16, further comprising providing biofeedback related to leg motions of the patient to a computerized training game system such that the leg motions control action in a computerized training game, encouraging the patient to perform training exercises.

22. The method of claim 21, wherein the computerized training game system includes a virtual reality display headset worn by the patient while performing training exercises.

* * * * *